(12) United States Patent
Lanahan et al.

(10) Patent No.: US 9,018,447 B2
(45) Date of Patent: Apr. 28, 2015

(54) METHODS FOR INCREASING STARCH CONTENT IN PLANTS

(75) Inventors: Michael B. Lanahan, Cary, NC (US); John Steffens, Chapel Hill, NC (US)

(73) Assignee: Agrivida, Inc., Medford, MA (US)

( * ) Notice: Subject to any disclaimer, the term of this patent is extended or adjusted under 35 U.S.C. 154(b) by 693 days.

(21) Appl. No.: 12/264,620

(22) Filed: Nov. 4, 2008

(65) Prior Publication Data

US 2009/0119800 A1    May 7, 2009

Related U.S. Application Data

(60) Provisional application No. 60/985,356, filed on Nov. 5, 2007.

(51) Int. Cl.
| | | |
|---|---|---|
| *C12N 15/82* | (2006.01) | |
| *C12N 9/00* | (2006.01) | |
| *C12N 15/00* | (2006.01) | |
| *C12N 15/09* | (2006.01) | |

(52) U.S. Cl.
CPC .............. *C12N 15/8245* (2013.01); *C12N 9/00* (2013.01)

(58) Field of Classification Search
CPC ...... C12N 15/82; C12N 15/8245; C12N 9/00; C12N 15/09; C12N 9/1294; C12N 15/113; C12N 15/1137
See application file for complete search history.

(56) References Cited

U.S. PATENT DOCUMENTS

| 5,912,415 A * | 6/1999 | Olszewski et al. ............. 800/298 |
| 2006/0150278 A1* | 7/2006 | Frohberg et al. ............. 800/284 |
| 2007/0250961 A1* | 10/2007 | Blaylock et al. ............. 800/283 |

FOREIGN PATENT DOCUMENTS

| WO | 0011144 | 3/2000 |
| WO | 02086112 | 10/2002 |
| WO | 03071860 | 9/2003 |
| WO | 2005030942 | 4/2005 |
| WO | 2005095618 | 10/2005 |
| WO | 2005097999 | 10/2005 |

OTHER PUBLICATIONS

Grennan Aleel K, "Regulation of Starch Metabolism in *Arabidopsis* Leaves", Plant Physiology, vol. 142, No. 4, (Dec. 2006) pp. 1343-1345.
Lloyd J R et al., "Leaf Starch degradation comes out of the shadows" Trends in Plant Science, Elsevier Science, Oxford GB, vol. 10, No. 3, (Mar. 1, 2005) pp. 130-137.
Scheidig Andreas et al., "Downregulation fo a chloroplast-targeted beta-amylase leads to a starch-excess phenotype in leaves", Plant Journal, vol. 30, No. 5 (Jun. 2002) pp. 581-591.
Niittyla Totte, et al., "A previously unknown maltose transporter essential for starch degradation in leaves", Science, vol. 303, No. 5654 (Jan. 2, 2004) pp. 87-89.
Smith Alison M., et al., "Starch mobilization in leaves", Journal of Experimental Botany, vol. 54, No. 382 (Jan. 1, 2003) pp. 577-583.
Asatsuma Satoru et al., "Involvement of alpha-amylase I-1 in starch degradation in rice chloroplasts", Plant and Cell Physiology, vol. 46, No. 6 (Jun. 2005) pp. 858-869.
Syngenta Participations AG, "International Search Report", PCT/US2008/082336, Feb. 17, 2009.
Syngenta Participations AG, "Written Opinion", PCT/US2008/082336, Feb. 17, 2009.
Matsuoka et al., "The promoters of two carboxylases in a C4 plant (maize) direct cell-specific, light-regulated expression in a C3 plant (rice)," The Plant Journal (1994) 6(3), 311-319.
Sattarzadeh et al., "Transgenic maize lines with cell-type specific expression of fluorescent proteins in plastids," Plant Biotechnology Journal (2010) 8, pp. 112-125.
Majeran et al, "Functional Differentiation of Bundle Sheath and Mesophyll Maize Chloroplasts Determined by Comparative Proteomics," The Plant Cell, vol. 17, 3111-3140, Nov. 2005.
Gudesblat et al., "Guard cell-specific inhibition of Arabidopsis MPK3 expression causes abnormal stomatal responses to abscisic acid and hydrogen peroxide," New Phytologist (2007) 173: 713-721.
Xu et al., "RNA Interference of Plant MAPK Cascades for Functional Studies," Methods in Molecular Biology, vol. 1171, pp. 91-103 (2014).
Stitt and Zeeman, "Starch turnover: pathways, regulation and role in growth," SciVerse ScienceDirect(2012) (15), 282-292.
Wu et al., "Modes of intercellular transcription factor movement in the *Arabidopsis* apex," The Company of Biologists Ltd. (2003) (130) 3735-3745.
Waigmann et al., "Direct functional assay for tobacco mosaic virus cell-to-cell movement protein and identification of a domain involved in increasing plasmodesmal permeability," Proc. Nat'l Acad. Sci. USA, vol. 91, 1433-1437, Feb. 1994.
Wolf et al., "Movement protein of Tobacco Mosaic Virus Modifies Plasmodesmatal Size Exclusion Limit," Science, New Series, vol. 246 (4928), 377-379, Oct. 1989.
Chen et al., "Identification of evolutionarily conserved amino acid residues in homeodomain of KNOX proteins for intercellular trafficking," Plant Signaling & Behavior 9, e28355, Feb. 2014 Landes Bioscience.
Edwards et al., "Compartmentation of photosynthesis in cells and tissues of C4 plants," Journal of Experimental Botany, vol. 52 (356) 577-590, Apr. 2001.

(Continued)

Primary Examiner — Brent T Page
(74) Attorney, Agent, or Firm — Volpe and Koenig, P.C.

(57) ABSTRACT

Methods and compositions for increasing the starch content in green tissues of a plant are provided. The method comprises down-regulating the activity of starch degradation enzymes in a plant. The resulting transgenic plants of the invention have increased starch content in green tissues and exhibit a starch excess phenotype. In one embodiment the method involves manipulating a monocot plant to down-regulate the activity of a starch degradation enzyme. The plants are useful for improving the yield of free sugars from plant biomass and increase dried green tissue storage stability.

14 Claims, No Drawings

(56) References Cited

OTHER PUBLICATIONS

Oparka et al., "Simple, but Not Branched, Plasmodesmata Allow the Nonspecific Trafficking of Proteins in Developing Tobacco Leaves," Cell, vol. 97, 743-754, Jun. 1999.

Crawford and Zambryski, "Subcellular localization determines the availability of non-targeted proteins to plasmodesmatal transport," Current Biology 2000, (10), 1032-1040, Aug. 2000.

Goodwin, "Molecular size limit for movement in the symplast of the *Elodea* leaf," Planta, (1983) (157), 124-130.

Sowinski et al., "On the mechanism of C4 photosynthesis intermediate exchange between Kranz mesophyll and bundle sheath cells in grasses," Journal of Experimental Botany, vol. 59 (6), 1137-1147, Mar. 2008.

Echeverria and Boyer, "Localization of Starch Biosynthetic and Degradative Enzymes in Maize Leaves," American Journal of Botany, vol. 73 (2), 167-171, Feb. 1986.

Majeran, et al., "Functional Differentiation of Bundle Sheath and Mesophyll Maize Chloroplasts Determined by Comparative Proteomics," The Plant Cell, vol. 17, 3111-3140, Nov. 2005.

Stahl and Simon, "Gated communities: apoplastic and symplastic signals converge at plasmodesmata to control cell fates," Journal of Experimental Botany, (2013) vol. 64 (17), 5237-5241.

* cited by examiner

METHODS FOR INCREASING STARCH CONTENT IN PLANTS

FIELD OF THE INVENTION

This invention relates to plant molecular biology, particularly to methods and compositions for increasing starch accumulation in plant tissues and the use of these plant tissues in commercial applications.

BACKGROUND OF THE INVENTION

Plant biomass is comprised of sugars and represents the greatest source of renewable hydrocarbon on earth. Unlike other renewable energy sources, biomass can be converted directly into liquid fuels. The two most common types of biofuels are ethanol (ethyl alcohol) and biodiesel. Ethanol is an alcohol, which can be produced by fermenting any biomass high in carbohydrates (starches, sugars, or celluloses). Once fermentable sugars have been obtained from the biomass material, these sugars can then be fermented to produce ethanol through a process similar to brewing beer. However, this enormous resource is under-utilized due to the fact sugars are locked in complex polymers, which are often referred to collectively as lignocellulose.

Conventional breakdown of the lignocellulose into monomers (monosaccharides) requires the biomass source material to be softened through chemical and/or physical pre-treatments. Enzymes may also be added that hydrolyze the polymeric forms of sugars contained in the biomass into monosaccharides. Subsequent fermentation can then be carried out utilizing both the 6-carbon and 5-carbon sugars to produce ethanol or other desired bio-products. Sugars generated from the degradation of plant biomass could provide plentiful, economically competitive feedstocks for fermentation into chemicals, plastics, feed additives and fuels.

Carbohydrates constitute the most abundant organic compounds on earth. They are principally found in plants as complex glucose polymers either in the form of cellulose or starch. Cellulose, hemicellulose and glucans make up many structural components of the plant cell wall and woody tissues. These structural components are often complexed with other molecules such as proteins, fats and lignin. Starch is utilized by the plant as a principle storage carbohydrate in seeds and grain consisting of essentially pure linked glucose polymers. Starches are found in many grains as well as in tubers and roots. Starch is a desirable storage carbohydrate due to the fact that it is compositionally simple and can be readily broken down by the plant for energy. Comparatively, lignocellulosic material is composed of glucose and/or several different sugars complexed with lignin. Starch is readily hydrolysable to monomer sugars via effective and inexpensive starch-hydrolysing enzymes whereas lignocellulosic material is neither readily hydrolysable nor relatively inexpensive to process. Carbohydrates are also found in abundance in the form of the simple disaccharide sucrose. Sucrose may be found in crops such as sugarcane, sugarbeets, and sweet sorghum. Unlike sucrose, starch is stable and can be stored in dehydrated form for long periods of time.

It would be desirable to produce a plant that is beneficial for the production of monomer sugars where a higher proportion of carbohydrate is in the form of starch. Methods for creating starch-rich plant biomass and methods for generating free sugars and oligosaccharides from plant biomass as well as use of these free sugars in a biomass conversion method are provided.

SUMMARY OF THE INVENTION

Compositions and methods for increasing the starch content in green tissues of plants are provided. Further provided, are methods in which these plants can be used in a biomass conversion method. The method involves independently or jointly down-regulating the endogenous activity of enzymes involved in the plant transitory starch degradation pathway. Down-regulation may be targeted constitutively throughout the plant or within preferred target tissues (i.e. stem, leaf etc.). The transgenic plants of the invention have increased starch content in green tissues and exhibit a starch excess phenotype. The biomass obtained from these transgenic plants can be converted to generate an enhanced level of free sugars that are useful in the downstream fermentation of free sugars into chemicals, plastics, feed additives and fuels. Also provided are methods of producing a self-processing plant with increased starch content in green tissues by further expressing starch processing enzymes that upon activation of the processing enzyme(s) (mesophilic, thermophilic, or hyperthermophilic) the plant or plant part is capable of self-processing the substrate upon which it acts to obtain the desired result.

DETAILED DESCRIPTION OF THE INVENTION

Overview

The article "a" and "an" are used herein to refer to one or more than one (i.e., to at least one) of the grammatical object of the article. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Methods and compositions for increasing the starch content in green tissues of a plant are provided. The method comprises down-regulating the activity of enzymes involved in the transitory starch degradation pathway in a plant. The resulting transgenic plants of the current invention have increased starch content in green tissues and exhibit a starch excess phenotype. Further provided, are methods of use for plants with increased starch content in green tissues.

Transgenic plants, seeds, plant tissues and plant parts are provided. It is recognized that the process may be controlled by the use of constitutive, tissue, temporal or chemically regulated promoters. The following embodiments can be carried out in either monocotyledon or dicotyledonous plants.

A method to increase starch in plant green tissue may be desirable across multiple industries for example but not limited to ethanol, animal feed, plastics, chemicals and other industrial applications. One embodiment of current application involves manipulating a plant to down-regulate the activity of one or more chloroplastic or cytosolic enzymes involved in the transitory starch degradation pathway, herein referred to as "starch degradation enzymes". The resultant plants of the invention have increased starch content in green tissues. Starch degradation enzymes include, but are not limited to chloroplastic alpha-amylase, glucan water dikinase, phosphoglucan water dikinase, limit dextrinase, isoamylase, chloroplastic beta-amylase, chloroplastic glucan phosphorylase, disproportionating enzyme, chloroplastic maltose transporter protein, chloroplastic glucose transporter protein, chloroplastic triose phosphate transporter protein, cytosolic transglucosidase, glucan phosphorylase, and hexokinase.

The methods of the invention find use in the integration of current practices for the cultivation of crop plants for the purpose of obtaining a commercially desired plant material with increased starch accumulation in the green tissues of the crop plants, and the use of the crop plant residues as a source of biomass for the production of fermentable sugars, or for agricultural and/or human consumption. The methods of the invention involve changing a plant from a sugar-storing plant to a starch-storing plant. The modified plants and plant parts can be used in the production of alcohol and yield increased ethanol by engineering the plant to accumulate starch.

As used herein, "crop plant" refers to any plant that is cultivated for the purpose of producing plant material sought after by man or animal for either oral consumption, or for utilization in an industrial, pharmaceutical, or commercial process. The invention may be applied to any variety of plants, including, but not limited to maize, wheat, rice, barley, soybean, cotton, sorghum, beans in general, rape/canola, alfalfa, flax, sunflower, safflower, millet, rye, sugarcane, sugar beet, cocoa, tea, tropical sugar beet, *Brassica*, cotton, coffee, sweet potato, flax, peanut, clover; vegetables such as lettuce, tomato, cucurbits, cassava, potato, carrot, radish, pea, lentils, cabbage, cauliflower, broccoli, Brussels sprouts, peppers, and pineapple; tree fruits such as citrus, apples, pears, peaches, apricots, walnuts, avocado, banana, and coconut; and flowers such as orchids, carnations and roses. Other plants useful in the practice of the invention include perennial grasses, such as switchgrass, prairie grasses, Indiangrass, Big bluestem grass, miscanthus and the like. It is recognized that mixtures of plants may be used.

As used herein, the term "energy crop" refers to crops that may be favorable to use in a biomass conversion method in converting plant biomass to fuels. This group comprises but is not limited to sugarcane, sugarbeet, sorghum, switchgrass, miscanthus, wheat, rice, oat, barley and maize.

As used herein, the term "plant part" or "plant tissue" includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like.

In one embodiment, the plant is an indeterminate plant. These varieties grow vegetatively for indefinite periods in temperate regions. An indeterminate plant can be engineered to accumulate starch in green tissues and can be grown until the first frost. At that time, the plant could be allowed to desiccate, harvested dry, and used for food, livestock feed, or in biomass conversion processes.

In another embodiment, the plant is a photoperiod sensitive plant. One example of a photoperiod sensitive plant would be a tropical maize variety which when grown in the Midwest (or comparable long day summer climates) the plant will grow tall and generate little or no ears of maize. This in turn allows the tropical maize variety to have a large amount of green tissue biomass and accumulate sugars mainly in the form of sucrose in the plant's stalks and leaves. The current invention would convert these sucrose-storing photoperiod sensitive plants into starch-storing plants. Thus, increasing the value of the photoperiod sensitive plant and its' biomass storage stability.

As used herein, "biomass" refers to useful biological material including a product of interest, which material is to be collected and is intended for further processing to isolate or concentrate the product of interest. "Biomass" may comprise the fruit or parts of it or seeds, leaves, or stems or roots where these are the parts of the plant that are of particular interest for the industrial purpose. "Biomass", as it refers to plant material, includes any structure or structures of a plant that contain or represent the product of interest.

An increase in starch accumulation may be desirable, for example, in a plant which is conserved by silage or drying. The term "harvest index" as defined herein refers to the ratio of biomass yield to the cumulative biomass at harvest. Two of the best energy crops today, cane and beets, in terms of harvest index, have limitations on storage stability, and have high moisture content at harvest. High moisture content has several disadvantages such as transportation costs for the harvest are higher since a greater proportion of the water needs to be moved with the crop. Storage stability is a significant issue, since there may be continued metabolism, or microbial contaminations that can lead to crop spoilage and sugar loss. Perishability of the crop has very different infrastructural implications for the movement, storage, and utilization of these types of agricultural products. An increase of the starch content would lead to a considerable increase of dry substance and storage stability.

One embodiment of the current application provides a method for converting a sucrose-storing plant to a starch-storing plant comprising inserting an expression cassette into a sucrose-storing plant cell comprising a polynucleotide wherein expression of the polynucleotide sequence decreases or inhibits the activity of one or more starch degradation enzymes selected from the group consisting of chloroplastic alpha-amylase, glucan water dikinase, phosphoglucan water dikinase, limit dextrinase, isoamylase, chloroplastic beta-amylase, chloroplastic glucan phosphorylase, disproportionating enzyme, chloroplastic maltose transporter protein (Mex1), chloroplastic glucose transporter protein, and chloroplastic triose phosphate transporter protein. Regeneration of transgenic plants from the plant cell of said sucrose-storing plant. The said polynucleotide would preferably be linked to an operable green tissues preferred promoter such as but not limited to the phosphoenolpyruvate carboxylase promoter. The resultant plant will have an advantage over conventional sucrose-storing plants in that the starch-storing plant will have a higher harvest index, longer storage stability, less moisture, less microbial contamination, decreased cost in transportation and more susceptible to drying down. As used herein, a "sucrose-storing" plant is any plant that contains high amounts of sucrose (stored or transitory) in its plant cells and plant parts this group may include but is not limited to energy crops.

Starch Biosynthesis and Degradation

Starch is one of the most abundant polymers produced in nature and is synthesized as a storage carbohydrate throughout the plant kingdom. In storage organs it serves as a long-term carbon reserve, whereas in photosynthetically competent tissues it is transiently accumulated to provide both reduced carbon and energy during periods unfavorable for photosynthesis. Starch is a desirable storage carbohydrate because it is compositionally simple compared to cellulosic material. Cellulosic material comprises several different sugars, complexed with lignin. Lignocellulose is extremely difficult to break down enzymatically. In contrast, starch is comprised of glucose and is readily hydrolysable to monomer sugars via effective and inexpensive starch-hydrolyzing enzymes. The accumulation of starch in green tissues and stems would provide a rich source for simple sugars in the plant biomass.

Starch degradation in green tissue involves multiple enzymes and transporters. Transitory starch is essentially converted in the chloroplast stroma to glucose, maltose and triose phosphate through the actions of starch degradation enzymes. These sugars are then transported from the chloroplast stroma to the cytosol via sugar transporters. Once in the cytosol these simple sugars will then be utilized in plant cellular metabolism.

One embodiment of the current application is to suppress or inactivate key starch degradation enzymes and transporters within the chloroplast stroma in order to accumulate starch within green tissues. Key cytosolic enzymes involved in the starch degradation pathway may also be suppressed or inactivated to increase the accumulation of starch in green tissue.

Starch comprises both linear (amylose) and branched (amylopectin) glucose polymers. Amylopectin from many, but not all plant sources contains phosphate-monoesters that are linked mainly to the C6 and C3 positions of glycosyl residues. The biochemical mechanism of starch phosphorylation has, however, only recently been elucidated. Transgenic potato plants (Lorberth et al (1998) *Nat Biotechnol.* 16(5):473-7) and the sex1 mutant of *Arabidopsis* (Yu et al. (2001) *Plant Cell* 13(8):1907-18) are deficient in a starch associated protein, which is herein referred to as R1, and they synthesize starch with decreased phosphate content. The purified recombinant R1-protein from potato is able to phosphorylate α-glucans (Ritte et al. (2002) *Proc Natl Acad Sci USA* 99(10):7166-71). It catalyses a dikinase-type reaction, liberating the γ-phosphate of ATP (resulting in the release of orthophosphate), but using the β-phosphate to phosphorylate glucosyl residues of the polyglucan. Because of this activity, the protein is considered a glucan, water dikinase (GWD) (Ritte et al. (2003) *Planta* 216(5):798-801).

Inhibition of the R1 gene which codes for an R1 protein from potatoes in transgenic potato plants results in a reduction of the phosphate content of the starch which can be isolated from the potato tubers (Lorberth et al.). Furthermore, Lorberth et al. showed that the R1 protein from *Solanum tuberosum* is capable of phosphorylating bacterial glycogen if the corresponding R1 cDNA is expressed in *E. coli* (Lorberth et al., Nature Biotech. 16, (1998), 473-477). Ritte et al. (Plant J. 21, (2000), 387-391) showed that the R1 protein from *Solanum tuberosum* binds reversibly to starch grains in potato plants, wherein the strength of binding to the starch grain depends on the metabolic status of the plant. In starch grain-bound form, the protein in potato plants mainly occurs in leaves which are kept in the dark. After the leaves are illuminated, however, the protein is mainly present in a soluble form which is not bound to starch grains.

The phosphorylation of starch strongly affects its in vivo degradability. This activity is indicated by the starch excess phenotype observed in leaves of GWD deficient potato or *Arabidopsis* plants (Lorberth et al., 1998, supra; Yu et al., 2001, supra). A reduction in the expression and/or activity of the R1 protein and its homologues in a plant or plant cell result in this starch excess phenotype, which means that a plant deficient in R1 activity is no longer capable of mobilizing the starch synthesized in its green tissues (transitory starch). Therefore, these plants show an accumulation of starch in their green tissues. By "green tissues" is intended all of the green structures in a plant, including leaves, stems, and unripened fruit. Starch that is accumulated in green tissues is referred to herein as "green starch."

This starch excess property can be assayed, e.g., as described in U.S. Patent Application Publication No. 2006/0236426, herein incorporated by reference. In particular, source leaves of the plants are kept in darkness for different time intervals and then stained with iodine in order to determine their starch content. Leaves of plants which cannot mobilize the transitory starch in the dark show a blue staining, or the blue staining in these leaves is stronger or staining is apparent after longer time intervals in the dark as compared to staining that may occur in leaves of corresponding wild-type plants.

Furthermore, the accumulation of transitory starch in the green tissues can also be tested by enzymatically determining the starch content in the leaves. This can be done, e.g. as described in Muller-Rober et al. (EMBO J. 11 (1992), 1229-1238). Green tissues of plants in which the activity of the one or more starch degradation enzymes are reduced preferably have an increased starch content of at least about 50%, at least about 75%, at least about 100%, at least about 150%, at least about 200%, at least about 250%, at least about 300%, at least about 350%, at least about 400%, at least 600%, or greater, when compared to green tissues of corresponding wild-type plants.

Inhibition of Starch Degradation Enzyme Activity

In the methods and compositions of the present invention, starch accumulation occurs in the green tissues of plants in which the activity of the starch degradation enzymes or homologues thereof are down-regulated. By down-regulating the activity, it is intended that the level of activity of the starch degradation protein or enzyme in a plant is decreased or completely suppressed in comparison to the activity in a corresponding control plant which has not been manipulated to decrease the activity of a starch degradation enzyme. The activity of the starch degradation enzyme, the target protein, is inhibited, reduced, or eliminated if the activity is less than 95%, less than about 90%, less than about 80%, less than about 70%, less than about 60%, less than about 50%, less than about 40%, less than about 30%, less than about 20%, less than about 10%, or is 100% less than the activity of the starch degradation enzyme in a plant that is not a mutant or that has not been genetically modified to inhibit the expression of a starch degradation enzyme. The activity of a starch degradation enzyme can be measured by measuring the starch content in the leaves of the plants. Methods for the measurement of starch content are available in the art. See, for example, Yu et al. (2001) *The Plant Cell* 13:1907-1918, herein incorporated by reference. R1 enzyme activity can be measured by methods set forth, for example, in Ritte et al. (2002) *Proc. Natl. Acad. Sci USA* 14:7166-7171, herein incorporated by reference. Likewise, levels of expression of the starch degradation enzymes can be directly measured by immunoblots demonstrating a reduction in a starch degradation enzyme in the plant, by Western blot analysis and the like.

Any method to reduce the activity of a starch degradation enzyme in a plant can be used in the practice of the methods of the invention. For example, the activity and/or level of the R1 protein can be reduced or eliminated by introducing into a plant a polynucleotide that inhibits the level or activity of the R1 protein. The polynucleotide may inhibit the expression or the translation of the messenger RNA. Likewise, down-regulation may be achieved by transforming the plant with a nucleic acid sequence that encodes a polypeptide that inhibits the transcription or translation of starch degradation enzyme, or that inhibits the activity of the starch degradation enzyme.

The terms "inhibit," "inhibition," "down-regulation" and "inhibiting" as used herein refers to any decrease in the expression or function of a target gene product, including any relative decrement in expression or function up to and including complete abrogation of expression or function of the target gene product. The term "expression" as used herein in the context of a gene product refers to the biosynthesis of that gene product, including the transcription and/or translation and/or assembly of the gene product. Inhibition of expression or function of a target gene product (i.e., a gene product of interest) can be in the context of a comparison between any two plants, for example, expression or function of a target gene product in a genetically altered plant versus the expression or function of that target gene product in a corresponding wild-type plant. Alternatively, inhibition of expression or function of the target gene product can be in the context of a comparison between plant cells, organelles, organs, tissues, or plant parts within the same plant or between plants, and includes comparisons between developmental or temporal stages within the same plant or between plants.

Methods for inhibiting or eliminating the expression of a gene in a plant are well known in the art, and any such method may be used in the methods of the present invention. Antisense constructs, complementary to at least a portion of the messenger RNA (mRNA) for the target sequence can be utilized. Antisense nucleotides are constructed to hybridize with the corresponding mRNA. Modifications of the antisense sequences may be made as long as the sequences hybridize to and interfere with expression of the corresponding mRNA. In this manner, antisense constructs having at least about 70%, at least about 80%, at least about 85% or higher sequence identity to the corresponding sense sequences may be used. Furthermore, portions of the antisense nucleotides may be used to disrupt the expression of the target gene. Generally, sequences of at least about 10 nucleotides, at least about 20 nucleotides, at least about 30 nucleotides, at least about 40 nucleotides, at least about 50 nucleotides, at least about 100 nucleotides, at least about 200 nucleotides, at least about 300, at least about 400, at least about 450, at least about 500, at least about 550, or greater may be used. Antisense methods are known in the art. See, for example, Sheehy et al. (1988) *Proc. Natl. Acad. Sci. USA* 85:8805-8809; and U.S. Pat. Nos. 5,107,065; 5,453,566; and 5,759,829); herein incorporated by reference.

Cosuppression may also be used to suppress the expression of the target gene. In this manner, a heterologous starch degradation enzyme sequence is expressed in a plant of interest in the sense orientation to suppress the expression of the endogenous starch degradation enzyme gene in the plant. Methods for cosuppression are known in the art. See, for example, Taylor (1997) *Plant Cell* 9:1245; Jorgensen (1990) *Trends Biotech.* 8(12):340-344; Jorgensen et al. (1996) *Plant Mol. Biol.* 31:957-973; Johansen and Carrington (2001) *Plant Physiol.* 126:930-938; Broin et al. (2002) *Plant Cell* 14:1417-1432; Stoutjesdijk et al (2002) *Plant Physiol.* 129:1723-1731; Yu et al. (2003) *Phytochemistry* 63:753-763; Flavell (1994) *Proc. Natl. Acad. Sci. USA* 91:3490-3496; Finnegan et al. (1994) *Bio/Technology* 12:883-888; Neuhuber et al. (1994) *Mol. Gen. Genet.* 244:230-241; and U.S. Pat. Nos. 5,034,323, 5,283,184, and 5,942,657; all of which are herein incorporated by reference.

Cosuppression involves transforming plants with a DNA construct comprising a promoter that drives expression in a plant operably linked to at least a portion of a polynucleotide that corresponds to the transcript of the gene of interest or the target gene. The nucleotide sequence is constructed or chosen to have substantial sequence identity to the sequence of the transcript of the endogenous gene, typically greater than about 60% sequence identity, more typically greater than about 80% sequence identity, more typically greater than about 90% sequence identity, and in some instances greater than about 95% sequence identity.

RNA interference (RNAi) can also be used to down-regulate starch degradation enzyme genes. See, generally, Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; and Montgomery et al. (1998) *Proc. Natl. Acad. Sci. USA* 95:15502-15507. In RNAi, long double-stranded RNAs (dsRNAs), typically >200 nucleotides, can be used to silence the expression of a target gene in a plant. Upon introduction, the long dsRNAs enter a cellular pathway that is commonly referred to as the RNA interference (RNAi) pathway. First, the dsRNAs get processed into 20-25 nucleotide (nt) small interfering RNAs (siRNAs) by an RNase III-like enzyme. These siRNAs assemble into endoribonuclease-containing complexes known as RNA-induced silencing complexes (RISCs), unwinding in the process. The siRNA strands subsequently guide the RISCs to complementary RNA molecules, where they cleave and destroy the cognate RNA. Cleavage of cognate RNA takes place near the middle of the region bound by the siRNA strand.

In this manner, double-stranded RNA (dsRNA) interference may be used. For dsRNA interference, a sense and an antisense RNA molecule that is fully or partially complementary to the sense RNA molecule are expressed in the same cell, resulting in inhibition of the expression of the corresponding endogenous messenger RNA.

The sense and antisense molecules can be expressed from a single or separate expression cassette. Alternatively, multiple plant lines transformed with the dsRNA interference expression cassette or expression cassettes are then screened to identify plant lines that show the greatest inhibition of starch degradation enzyme expression. Methods for using dsRNA interference to inhibit the expression of endogenous plant genes are described in Waterhouse et al. (1998) *Proc. Natl. Acad. Sci. USA* 95:13959-13964, Liu et al. (2002) *Plant Physiol.* 129:1732-1743, and WO 99/49029, WO 99/53050, WO 99/61631, and WO 00/49035; each of which is herein incorporated by reference.

In some embodiments of the invention, inhibition of the expression of a starch degradation enzyme may be obtained by hairpin RNA (hpRNA) interference or intron-containing hairpin RNA (ihpRNA) interference. A short hairpin RNA (shpRNA) is a sequence of RNA that makes a tight hairpin turn that can be used to silence gene expression. These methods are highly efficient at inhibiting the expression of endogenous genes. See, Waterhouse and Helliwell (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz (2000) *Proc. Natl. Acad. Sci. USA.* 97:4985-4990; Stoutjesdijk et al. (2002) *Plant Physiol.* 129:1723-1731; and Waterhouse and Helliwell (2003) *Nat. Rev. Genet.* 4:29-38. Methods for using hpRNA interference to inhibit or silence the expression of genes are described, for example, in Chuang and Meyerowitz (2000) *Proc. Natl. Acad. Sci. USA* 97:4985-4990; Stoutjesdijk et al. (2002) *Plant Physiol.* 129:1723-1735; Waterhouse and Helliwell (2003) *Nat. Rev. Genet.* 4:29-38; Pandolfini et al. *BMC Biotechnology* 3:7, and U.S. Patent Publication No. 20030175965; each of which is herein incorporated by reference. A transient assay for the efficiency of hpRNA constructs to silence gene expression in vivo has been described by Panstruga et al. (2003) *Mol. Biol. Rep.* 30:135-140, herein incorporated by reference.

Interfering hairpin RNA (ihpRNA) may also be used in the methods of the invention. ihpRNA have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, thus increasing the efficiency of interference. See, for example, Smith et al. (2000) *Nature* 407:319-320. Methods for using ihpRNA interference to inhibit the expression of endogenous plant genes are described, for example, in Smith et al. (2000) *Nature* 407:319-320; Wesley et al. (2001) *Plant J.* 27:581-590; Wang and Waterhouse (2001) *Curr. Opin. Plant Biol.* 5:146-150; Waterhouse and Helliwell (2003) *Nat. Rev. Genet.* 4:29-38; Helliwell and Waterhouse (2003) *Methods* 30:289-295, and U.S. Patent Publication No. 20030180945, each of which is herein incorporated by reference. See also WO 02/00904 where the hpRNA is designed such that the loop region determines the specificity of the RNA interference.

In some embodiments of the invention, RNA interference by expression of a gene encoding a micro RNA (miRNA) may be used. miRNAs are regulatory agents consisting of about 22 ribonucleotides. miRNA are highly efficient at inhibiting the expression of endogenous genes. See, for example Javier et al. (2003) *Nature* 425: 257-263, herein incorporated by reference. For miRNA interference, the expression cassette is designed to express an RNA molecule that is modeled on an endogenous miRNA gene. The miRNA gene encodes an RNA that forms a hairpin structure containing about a 22-nucleotide sequence that is complementary to R1. For example, for suppression of R1 expression, the 22-nucleotide sequence is selected from a starch degradation enzyme transcript sequence and contains 22 nucleotides of said starch degradation enzyme sequence in sense orientation and 21 nucleotides of a corresponding antisense sequence that is complementary to the sense sequence.

Other methods for down-regulating the activity of a target protein include virus-induced gene silencing (Burton et al. (2000) *Plant Cell* 12:691-705; and Baulcombe (1999) *Curr. Op. Plant Bio.* 2:109-113); ribozymes (Steinecke et al. (1992) *EMBO J.* 11:1525; and Perriman et al. (1993) *Antisense Res. Dev.* 3:253); oligonucleotide-mediated targeted modification (e.g., WO 03/076574 and WO 99/25853); Zn-finger targeted molecules (e.g., WO 01/52620; WO 03/048345; and WO 00/42219); transposon tagging (Maes et al. (1999) *Trends Plant Sci.* 4:90-96; Dharmapuri and Sonti (1999) *FEMS Microbiol. Lett.* 179:53-59; Meissner et al. (2000) *Plant J.* 22:265-274; Phogat et al. (2000) J. Biosci. 25:57-63; Walbot (2000) *Curr. Opin. Plant Biol.* 2:103-107; Gai et al. (2000) *Nucleic Acids Res.* 28:94-96; Fitzmaurice et al. (1999) *Genetics* 153:1919-1928; Bensen et al. (1995) *Plant Cell* 7:75-84; Mena et al. (1996) *Science* 274:1537-1540; and U.S. Pat. No. 5,962,764); each of which is herein incorporated by reference.

Furthermore, nucleic acid molecules encoding antibodies specifically recognizing a starch degradation enzyme protein, or homologues thereof, according to the invention in a plant cell, i.e. specific fragments or epitopes of such a protein, can be used for inhibiting the activity of this protein. These antibodies can be monoclonal antibodies, polyclonal antibodies or synthetic antibodies as well as fragments of antibodies, such as Fab, Fv or scFv fragments etc. Monoclonal antibodies can be prepared, for example, by the techniques as originally described in Kohler and Milstein (Nature 256 (1975), 495) and Galfre (Meth. Enzymol. 73 (1981) 3), which comprise the fusion of mouse myeloma cells to spleen cells derived from immunized mammals. Furthermore, antibodies or fragments thereof to the aforementioned peptides can be obtained by using methods which are described, e.g., in Harlow and Lane "Antibodies, A Laboratory Manual", CSH Press, Cold Spring Harbor, 1988. Expression of antibodies or antibody-like molecules in plants can be achieved by methods well known in the art, for example, full-size antibodies (During, Plant. Mol. Biol. 15 (1990), 281-293; Hiatt, Nature 342 (1989), 469-470; Voss, Mol. Breeding 1 (1995), 39-50), Fab-fragments (De Neve, Transgenic Res. 2 (1993), 227-237), scFvs (Owen, Bio/Technology 10 (1992), 790-794; Zimmermann, Mol. Breeding 4 (1998), 369-379; Tavladoraki, Nature 366 (1993), 469-472) and dAbs (Benvenuto, Plant Mol. Biol. 17 (1991), 865-874) have been successfully expressed in tobacco, potato (Schouten, FEBS Lett. 415 (1997), 235-241) or *Arabidopsis*, reaching expression levels as high as 6.8% of the total protein (Fiedler, Immunotechnology 3 (1997), 205-216).

In addition, nucleic acid molecules encoding a mutant form of the enzyme according to the invention can be used to interfere with the activity of the wild-type protein. Such a mutant form preferably has lost its activity and may be derived from the corresponding wild-type protein by way of amino acid deletion(s), substitution(s), and/or additions in the amino acid sequence of the protein. Mutant forms of such proteins may show, in addition to the loss of activity, an increased substrate affinity and/or an elevated stability in the cell, for instance, due to the incorporation of amino acids that stabilize proteins in the cellular environment. These mutant forms may be naturally occurring or, as preferred, genetically engineered mutants.

It is further contemplated that the methods of the invention can be used with other methods for increasing and/or utilizing the starch content of a plant. It is recognized that any mechanism of decreasing the phosphorylation of starch can lead to accumulation of starch in green tissues, including inhibiting phosphoglucan water dikinase (Kotting et al. (2005) *Plant Physiology* 137:242-252). Other methods include up-regulating the expression of enzymes involved in the synthesis of starch, for example, ADP-glucose phosphorylase.

Starch Degradation Enzymes' Nucleotide Sequences

The nucleotide sequences for starch degradation enzymes have been identified in *Arabidopsis* leaves See, alpha-amylase (EC 3.2.1.1), glucan water dikinase (EC 2.7.9.4), Phosphoglucan water dikinase (EC 2.7.9.4), limit dextrinase (EC 3.2.1.142), Isoamylase (EC 3.2.1.68 and EC3.2.1.68), beta-amylase (EC 3.2.1.2), glucan phosphorylase (EC2.4.1.1) and disproportionating enzyme (EC 2.4.1.25). It is recognized that these sequences may be used to down-regulate or suppress expression of the target protein in any plant. However, if additional plant-specific sequence is needed, it can be obtained by hybridization or PCR using the nucleotide sequences noted above.

The nucleotide sequences for R1 proteins from other plants are known in the art. See, for example SEQ ID NO:1 of US Application Publication No. 2006/0282917 (*Zea mays*); SEQ ID NOs:1, 4, 5, 6, 7, and 9 of U.S. Pat. No. 7,122,727 (wheat); herein incorporated by reference. It is recognized that these sequences may be used to down-regulate or suppress expression of the R1 protein in any plant. However, if additional plant-specific sequence is needed (e.g, an R1 homolog), it can be obtained by hybridization or PCR using sequences based on the R1 nucleotide sequences noted above.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art. See, for example, Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York).

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

By "hybridizing to" or "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, N.Y. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone nucleotide sequences that are homologues of reference nucleotide sequences of the present invention; a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.

Plant Expression Cassettes

The compositions of the invention may additionally contain nucleic acid sequences for transformation and expression in a plant of interest. The nucleic acid sequences may be present in DNA constructs or expression cassettes. "Expression cassette" as used herein means a nucleic acid molecule capable of directing expression of a particular nucleotide sequence in an appropriate host cell, comprising a promoter operatively linked to the nucleotide sequence of interest (i.e., an R1 inhibiting polynucleotide) which is operatively linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. Additionally, the promoter can also be specific to a particular tissue or organ or stage of development.

The present invention encompasses the transformation of plants with expression cassettes capable of expressing polynucleotides that reduce or eliminate the activity of one or more starch degradation enzymes. The expression cassette will include in the 5'-3' direction of transcription, a transcriptional and translational initiation region (i.e., a promoter) and a polynucleotide of interest, i.e., a polynucleotide capable of directly or indirectly (i.e. via expression of a protein product) reducing or eliminating the activity of one or more starch degradation enzymes. The expression cassette may optionally comprise a transcriptional and translational termination region (i.e. termination region) functional in plants. In some embodiments, the expression cassette comprises a selectable marker gene to allow for selection for stable transformants. Expression constructs of the invention may also comprise a leader sequence and/or a sequence allowing for inducible expression of the polynucleotide of interest. See, Guo et al. (2003) Plant J. 34:383-92 and Chen et al. (2003) Plant J. 36:731-40 for examples of sequences allowing for inducible expression.

The regulatory sequences of the expression construct are operably linked to the polynucleotide of interest. By "operably linked" is intended a functional linkage between a promoter and a second sequence wherein the promoter sequence initiates and mediates transcription of the DNA sequence corresponding to the second sequence. Generally, operably linked means that the nucleotide sequences being linked are contiguous.

Any promoter capable of driving expression in the plant of interest may be used in the practice of the invention. The promoter may be native or analogous or foreign or heterologous to the plant host. The terms "heterologous" and "exogenous" when used herein to refer to a nucleic acid sequence (e.g. a DNA or RNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" nucleic acid (e.g. DNA) sequence is a nucleic acid (e.g. DNA or RNA) sequence naturally associated with a host cell into which it is introduced.

The choice of promoters to be included depends upon several factors, including, but not limited to, efficiency, selectability, inducibility, desired expression level, and cell- or tissue-preferential expression. It is a routine matter for one of skill in the art to modulate the expression of a sequence by appropriately selecting and positioning promoters and other regulatory regions relative to that sequence.

Some suitable promoters initiate transcription only, or predominantly, in certain cell types. Thus, as used herein a cell type- or tissue-preferential promoter is one that drives expression preferentially in the target tissue, but may also lead to some expression in other cell types or tissues as well. It is understood that some promoters that show preferential targeting of expression in target tissues may also exhibit "leaky" expression in non-preferential targeted tissues. One example may be a promoter whose expression profile shows preferential expression in maize seed however also exhibits strong expression in mature leaf tissue. Methods for identifying and characterizing promoter regions in plant genomic DNA include, for example, those described in the following references: Jordano, et al., Plant Cell, 1:855-866 (1989); Bustos, et al., Plant Cell, 1:839-854 (1989); Green, et al., EMBO J. 7, 4035-4044 (1988); Meier, et al., Plant Cell, 3, 309-316 (1991); and Zhang, et al., Plant Physiology 110: 1069-1079 (1996).

Promoters active in photosynthetic tissue in order to drive transcription in green tissues such as leaves and stems are of particular interest for the present invention. Most suitable are promoters that drive expression only or predominantly in such tissues. The promoter may confer expression constitutively throughout the plant, or differentially with respect to the green tissues, or differentially with respect to the developmental stage of the green tissue in which expression occurs, or in response to external stimuli.

Examples of such promoters include the ribulose-1,5-bis-phosphate carboxylase (RbcS) promoters such as the RbcS promoter from eastern larch (*Larix laricina*), the pine cab6 promoter (Yamamoto et al. (1994) Plant Cell Physiol. 35:773-778), the Cab-1 gene promoter from wheat (Fejes et al. (1990) Plant Mol. Biol. 15:921-932), the CAB-1 promoter from spinach (Lubberstedt et al. (1994) Plant Physiol. 104:997-1006), the cab1R promoter from rice (Luan et al. (1992) Plant Cell 4:971-981), the pyruvate orthophosphate dikinase (PPDK) promoter from maize (Matsuoka et al. (1993) Proc Natl Acad Sci USA 90:9586-9590), the tobacco Lhcb1*2 promoter (Cerdan et al. (1997) Plant Mol. Biol. 33:245-255), the *Arabidopsis thaliana* SUC2 sucrose-H+ symporter promoter (Truernit et al. (1995) Planta 196:564-570), and thylakoid membrane protein promoters from spinach (psaD, psaF, psaE, PC, FNR, atpC, atpD, cab, rbcS. Other promoters that drive transcription in stems, leafs and green tissue are described in U.S. Patent Publication No. 2007/0006346, herein incorporated by reference in its entirety.

In some other embodiments of the present invention, inducible promoters may be desired. Inducible promoters drive transcription in response to external stimuli such as chemical agents or environmental stimuli. For example, inducible promoters can confer transcription in response to hormones such as gibberellic acid or ethylene, or in response to light or drought. Senescent inducible promoters may also be used in the current invention to suppress starch degradation enzymes at specific developmental stages of the plant as well as delay leaf senescence. One example would be to inhibit or suppress the starch degradation enzyme in maize post-harvest. Once the ear is harvested a senescence promoter (i.e. IPT) would then delay senescence in the plant. This will allow the plant to stay green longer the senescence promoter at the same time can drive inhibition or suppression of the starch degradation enzyme therefore creating a starch sink in the chloroplasts of green tissue. This combination may then increase the amount of starch in green tissue as well as allow for a method to not disrupt fruit development.

A variety of transcriptional terminators are available for use in expression cassettes. These are responsible for the termination of transcription beyond the transgene and correct mRNA polyadenylation. The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Appropriate transcriptional terminators are those that are known to function in plants and include the CAMV 35S terminator, the tml terminator, the nopaline synthase terminator and the pea rbcs E9 terminator. These can be used in both monocotyledons and dicotyledons. In addition, a gene's native transcription terminator may be used.

Generally, the expression cassette will comprise a selectable marker gene for the selection of transformed cells. Selectable marker genes are utilized for the selection of transformed cells or tissues.

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop. 1: 1183-1200 (1987)). In the same experimental system, the intron from the maize bronze 1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693-8711 (1987); Skuzeski et al. Plant Molec. Biol. 15: 65-79 (1990)). Other leader sequences known in the art include but are not limited to: picomavirus leaders, for example, EMCV leader (Encephalomyocarditis 5' noncoding region) (Elroy-Stein, O., Fuerst, T. R., and Moss, B. PNAS USA 86:6126-6130 (1989)); potyvirus leaders, for example, TEV leader (Tobacco Etch Virus) (Allison et al., 1986); MDMV leader (Maize Dwarf Mosaic Virus); Virology 154: 9-20); human immunoglobulin heavy-chain binding protein (BiP) leader, (Macejak, D. G., and Samow, P., Nature 353: 90-94 (1991); untranslated leader from the coat protein mRNA of alfalfa mosaic virus (AMV RNA 4), (Jobling, S. A., and Gehrke, L., Nature 325:622-625 (1987); tobacco mosaic virus leader (TMV), (Gallie, D. R. et al., Molecular Biology of RNA, pages 237-256 (1989); and Maize Chlorotic Mottle Virus leader (MCMV) (Lommel, S. A. et al., Virology 81:382-385 (1991). See also, Della-Cioppa et al., Plant Physiology 84:965-968 (1987).

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104-15109 (1988)). These signal sequences can be fused to heterologous gene products to effect the import of heterologous products into the chloroplast (van den Broeck, et al. Nature 313: 358-363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized. See also, the section entitled "Expression With Chloroplast Targeting" in Example 37 of U.S. Pat. No. 5,639,949.

The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

In order to ensure the localization in the plastids it is conceivable to use one of the following transit peptides: of the plastidic Ferredoxin: NADP+ oxidoreductase (FNR) of spinach which is enclosed in Jansen et al. (Current Genetics 13 (1988), 517-522). In particular, the sequence ranging from the nucleotides −171 to 165 of the cDNA sequence disclosed therein can be used, which comprises the 5' non-translated region as well as the sequence encoding the transit peptide. Another example is the transit peptide of the waxy protein of maize including the first 34 amino acid residues of the mature waxy protein (Klosgen et al., Mol. Gen. Genet. 217 (1989), 155-161). It is also possible to use this transit peptide without the first 34 amino acids of the mature protein. Furthermore, the signal peptides of the ribulose bisphosphate carboxylase small subunit (Wolter et al., Proc. Natl. Acad. Sci. USA 85 (1988), 846-850; Nawrath et al., Proc. Natl. Acad. Sci. USA 91 (1994), 12760-12764), of the NADP malat dehydrogenase (Galiardo et al., Planta 197 (1995), 324-332), of the glutathione reductase (Creissen et al., Plant J. 8 (1995), 167-175) or of the R1 protein Lorberth et al. (Nature Biotechnology 16, (1998), 473-477) can be used.

Plant Transformation

Once a starch degradation enzyme inhibiting nucleic acid sequence has been cloned into an expression system, it is transformed into a plant cell. The receptor and target expression cassettes of the present invention can be introduced into the plant cell in a number of art-recognized ways. The term "introducing" in the context of a polynucleotide, for example, a nucleotide construct of interest, is intended to mean presenting to the plant the polynucleotide in such a manner that the polynucleotide gains access to the interior of a cell of the plant. Where more than one polynucleotide is to be introduced, these polynucleotides can be assembled as part of a single nucleotide construct, or as separate nucleotide constructs, and can be located on the same or different transformation vectors. Accordingly, these polynucleotides can be introduced into the host cell of interest in a single transformation event, in separate transformation events, or, for example, in plants, as part of a breeding protocol. The methods of the invention do not depend on a particular method for introducing one or more polynucleotides into a plant, only that the polynucleotide(s) gains access to the interior of at least one cell of the plant. Methods for introducing polynucleotides into plants are known in the art including, but not limited to, transient transformation methods, stable transformation methods, and virus-mediated methods.

"Transient transformation" in the context of a polynucleotide is intended to mean that a polynucleotide is introduced into the plant and does not integrate into the genome of the plant.

By "stably introducing" or "stably introduced" in the context of a polynucleotide introduced into a plant is intended the introduced polynucleotide is stably incorporated into the plant genome, and thus the plant is stably transformed with the polynucleotide.

"Stable transformation" or "stably transformed" is intended to mean that a polynucleotide, for example, a nucleotide construct described herein, introduced into a plant integrates into the genome of the plant and is capable of being inherited by the progeny thereof, more particularly, by the progeny of multiple successive generations.

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the npt11 gene, which confers resistance to kanamycin and related antibiotics (Messing & Vierra. Gene 19: 259-268 (1982); Bevan et al., Nature 304:184-187 (1983)), the bar gene, which confers resistance to the herbicide phosphinothricin (White et al., Nucl. Acids Res 18: 1062 (1990), Spencer et al. Theor. Appl. Genet 79: 625-631 (1990)), the hph gene, which confers resistance to the antibiotic hygromycin (Blochinger & Diggelmann, Mol Cell Biol 4: 2929-2931), and the dhfr gene, which confers resistance to methatrexate (Bourouis et al., EMBO J. 2(7): 1099-1104 (1983)), the EPSPS gene, which confers resistance to glyphosate (U.S. Pat. Nos. 4,940,935 and 5,188,642), and the mannose-6-phosphate isomerase gene, which provides the ability to metabolize mannose (U.S. Pat. Nos. 5,767,378 and 5,994,629).

Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus Agrobacterium can be utilized to transform plant cells. Below are descriptions of representative techniques for transforming both dicotyledonous and monocotyledonous plants, as well as a representative plastid transformation technique.

Many vectors are available for transformation using *Agrobacterium tumefaciens*. These typically carry at least one T-DNA border sequence and include vectors such as pBIN19 (Sevan, Nucl. Acids Res. (1984)). For the construction of vectors useful in *Agrobacterium* transformation, see, for example, US Patent Application Publication No. 2006/0260011, herein incorporated by reference.

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on *Agrobacterium* include transformation via particle bombardment, protoplast uptake (e.g. PEG and electroporation) and microinjection. The choice of vector depends largely on the preferred selection for the species being transformed. For the construction of such vectors, see, for example, US Application No. 20060260011, herein incorporated by reference.

For expression of a nucleotide sequence of the present invention in plant plastids, plastid transformation vector pPH143 (WO 97/32011, example 36) is used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

Transformation techniques for dicotyledons are well known in die art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J. 3: 2717-2722 (1984), Potrykus et al., Mol. Gen. Genet. 199: 169-177 (1985), Reich et al., Biotechnology 4: 1001-1004 (1986), and Klein et al., Nature 327: 70-73 (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest (e.g. pCIB200 or pCIB2001) to an appropriate *Agrobacterium* strain which may depend of the complement of vir genes carried by the host *Agrobacterium* strain either on a co-resident Ti plasmid or chromosomally (e.g. strain CIB542 for pCIB200 and pCIB2001 (Uknes et al. Plant Cell 5: 159-169 (1993)). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Hofgen &. Willmitzer, Nucl. Acids Res. 16: 9877 (1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both of these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093-1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603-618 (1990)) and Fromm et al. (Biotechnology 8: 833-839 (1990)) have published techniques for transformation of A188-derived maize line using particle bombardment. Furthermore, WO 93/07278 and Koziel et al. (Biotechnology 11: 194-200 (1993)) describe techniques for the transformation of elite inbred lines of maize by particle bombardment. This technique utilizes immature maize embryos of 1.5-2.5 mm length excised from a maize ear 14-15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. Plant Cell Rep 7: 379-384 (1988); Shimamoto et al. Nature 338: 274-277 (1989); Datta et al. Biotechnology 8: 736-740 (1990)). Both types are also routinely transformable using particle bombardment (Christou et al. Biotechnology 9: 957-962 (1991)). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of *Dactylis* and wheat. Furthermore, wheat transformation has been described by Vasil et al. (Biotechnology 10: 667-674 (1992)) using particle bombardment into cells of type C long-term regenerable callus, and also by Vasil et al. (Biotechnologyl 11:1553-1558 (1993)) and Weeks et al. (Plant Physiol. 102: 1077-1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75-1 mm in length) are plated onto MS medium with 3% sucrose (Murashiga & Skoog, Physiologia Plantarum 15: 473-497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2-3 hours and are then bombarded. Twenty embryos per target plate is typical, although not critical. An appropriate gene-carrying plasmid (such as pCIB3064 or pSOG35) is precipitated onto micrometer size gold particles using standard procedures. Each plate of embryos is shot with the DuPont BIOLISTICS® helium device using a burst pressure of about 1000 psi using a standard 80 mesh screen. Alter bombardment, the embryos are placed back into the dark to recover for about 24 hours (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Transformation of monocotyledons using *Agrobacterium* has also been described. See, WO 94/00977 and U.S. Pat. No. 5,591,616, both of which are incorporated herein by reference. See also, Negrotto et al., Plant Cell Reports 19: 798-803 (2000), incorporated herein by reference.

For example, rice (*Oryza sativa*) can be used for generating transgenic plants. Various rice cultivars can be used (Hiei et al., 1994, Plant Journal 6:271-282; Dong et al., 1996, Molecular Breeding 2:267-276; Hiei et al., 1997, Plant Molecular Biology, 35:205-218). Also, the various media constituents described below may be either varied in quantity or substituted. Embryogenic responses are initiated and/or cultures are established from mature embryos by culturing on MS-CIM medium (MS basal salts, 4.3 g/liter; B5 vitamins (200×), 5 ml/liter; Sucrose, 30 g/liter; proline, 500 mg/liter; glutamine, 500 mg/liter; casein hydrolysate, 300 mg/liter; 2,4-D (1 mg/ml), 2 ml/liter; adjust pH to 5.8 with 1 N KOH; Phytagel, 3 g/liter). Either mature embryos at the initial stages of culture response or established culture lines are inoculated and co-cultivated with the *Agrobacterium tumefaciens* strain LBA4404 (*Agrobacterium*) containing the desired vector construction. *Agrobacterium* is cultured from glycerol stocks on solid YPC medium (100 mg/L spectinomycin and any other appropriate antibiotic) for about two days at 28° C. *Agrobacterium* is re-suspended in liquid MS-CIM medium. The *Agrobacterium* culture is diluted to an OD600 of 0.2-0.3 and acetosyringone is added to a final concentration of 200 µM. Acetosyringone is added before mixing the solution with the rice cultures to induce *Agrobacterium* for DNA transfer to the plant cells. For inoculation, the plant cultures are immersed in the bacterial suspension. The liquid bacterial suspension is removed and the inoculated cultures are placed on co-cultivation medium and incubated at 22° C. for two days. The cultures are then transferred to MS-CIM medium with Ticarcillin (400 mg/liter) to inhibit the growth of *Agrobacterium*. For constructs utilizing the PMI selectable marker gene (Reed et al., In Vitro Cell. Dev. Biol.-Plant 37:127-132), cultures are transferred to selection medium containing Mannose as a carbohydrate source (MS with 2% Mannose, 300 mg/liter Ticarcillin) after 7 days, and cultured for 3-4 weeks in the dark. Resistant colonies are then transferred to regeneration induction medium (MS with no 2,4-D, 0.5 mg/liter IAA, 1 mg/liter zeatin, 200 mg/liter timentin 2% Mannose and 3% Sorbitol) and grown in the dark for 14 days. Proliferating colonies are then transferred to another round of regeneration induction media and moved to the light growth room. Regenerated shoots are transferred to GA7 containers with GA7-1 medium (MS with no hormones and 2% Sorbitol) for 2 weeks and then moved to the greenhouse when they are large enough and have adequate roots. Plants are transplanted to soil in the greenhouse (To generation) grown to maturity, and the $T_1$ seed is harvested.

The plants obtained via transformation with a nucleic acid sequence of the present invention can be any of a wide variety of plant species, including those of monocots and dicots; however, the plants used in the method of the invention are preferably selected from the list of agronomically important target crops set forth supra. The expression of a gene of the present invention in combination with other characteristics important for production and quality can be incorporated into plant lines through breeding. Breeding approaches and techniques are known in the art. See, for example, Welsh J. R., Fundamentals of Plant Genetics and Breeding, John Wiley & Sons, NY (1981); Crop Breeding, Wood D. R. (Ed.) American Society of Agronomy Madison, Wis. (1983); Mayo O., The Theory of Plant Breeding, Second Edition, Clarendon Press, Oxford (1987); Singh, D. P., Breeding for Resistance to Diseases and insect Pests, Springer-Verlag, NY (1986); and Wricke and Weber, Quantitative Genetics and Selection Plant Breeding, Walter de Gruyter and Co., Berlin (1986).

For the transformation of plastids, seeds of *Nicotiana tabacum* c.v. "Xanthienc" are germinated seven per plate in a 1" circular array on T agar medium and bombarded 12-14 days after sowing with 1 um tungsten particles (M10, Biorad, Hercules, Calif.) coated with DNA from plasmids pPH143 and pPH145 essentially as described (Svab, Z. and Maliga, P. (1993) PNAS 90, 913-917). Bombarded seedlings are incubated on T medium for two days after which leaves are excised and placed abaxial side up in bright light (350-500 umol photons/m$^2$/s) on plates of RMOP medium (Svab. Z., Hajdukiewicz, P. and Maliga, P. (1990) PNAS 87, 8526-8530) containing 500 ug/ml spectinomycin dihydrochloride (Sigma, St. Louis, Mo.). Resistant shoots appearing underneath, the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) Molecular Cloning: A Laboratory Manual, Cold Spring Harbor Laboratory, Cold Spring Harbor). BamHI/EcoRI-digested total cellular DNA (Mettler, I. J. (1987) Plant Mol Biol Reporter 5, 346349) is separated on 1% Tris-borate (TBE) agarose gels, transferred to nylon membranes (Amersham) and probed with .sup.32P-labeled random primed DNA sequences corresponding to a 0.7 kb BamHI/HindIII DNA fragment from pC8 containing a portion of the rps 7/12plastid targeting sequence. Homoplasmic shoots are rooted aseptically on spectinomycin-containing MS/IBA medium (McBride, K. E. et al. (1994) PNAS 91, 7301-7305) and transferred to the greenhouse.

The genetic properties engineered into the transgenic seeds and plants described above are passed on by sexual reproduction or vegetative growth and can thus be maintained and propagated in progeny plants. Generally, maintenance and propagation make use of known agricultural methods developed to fit specific purposes such as tilling, sowing or harvesting.

Use of the advantageous genetic properties of the transgenic plants and seeds according to the invention can further be made in plant breeding. Depending on the desired properties, different breeding measures are taken. The relevant techniques are well known in the art and include but are not limited to hybridization, inbreeding, backcross breeding, multi-line breeding, variety blend, interspecific hybridization, aneuploid techniques, etc. Thus, the transgenic seeds and plants according to the invention can be used for the breeding of improved plant lines that, for example, increase the effectiveness of conventional methods such as herbicide or pesticide treatment or allow one to dispense with said methods due to their modified, genetic properties.

Biomass Conversion

Plants transformed according to the present invention provide a means of increasing ethanol yields, reducing pretreatment costs, by reducing acid/heat pretreatment requirements for saccharification of biomass; and/or reducing other plant production and processing costs, such as by allowing multi-applications and isolation of commercially valuable by-products Transgenic plants can be harvested as known in the art. For example, current techniques may cut corn stover at the same time as the grain is harvested, but leave the stover lying in the field for later collection. However, dirt collected by the stover can interfere with ethanol production from lignocellulosic material. One embodiment provides a method in which transgenic plants are cut, collected, stored, and transported so as to minimize soil contact. In addition to minimizing interference from dirt with ethanol production, this method can result in reduction in harvest and transportation costs.

Pretreatment.

Conventional methods Include physical, chemical, and/or biological pretreaments. For example, physical pretreatment techniques can include one or more of various types of milling, crushing, irradiation, steaming/steam explosion, and hydrothermolysis. Chemical pretreatment techniques can include acid, alkaline, organic solvent, ammonia, sulfur dioxide, carbon dioxide, and pH-controlled hydrothermolysis. Biological pretreatment techniques can involve applying lignin-solubilizing microorganisms (T.-A. Hsu, "Handbook on Bioethanol. Production and Utilization", C. E. Wyman (Ed.), 1996, Taylor & Francis: Washington, D.C., 179-212; P. Ghosh and A. Singh, A., Adv. Appl. Microbiol., 1993, 39: 295-333; J. D. McMillan, in "Enzymatic Conversion of Biomass for Fuels Production", M. Himmel et al., (Eds.), 1994, Chapter 15, ACS Symposium Series 566, American Chemical Society; B. Hahn-Hagerdal, Enz. Microb. Tech., 1996, 18: 312-331; and L. Vallander and K. E. L. Eriksson, Adv. Biochem. Eng./Biotechnol., 1990, 42: 63-95). The purpose of the pretreatment step is to break down the lignin and carbohydrate structure to make the cellulose fraction accessible to cellulolytic enzymes.

Saccharification.

In saccharification (or enzymatic hydrolysis), lignocellulose is converted into fermentable sugars by lignocellulolytic enzymes present in the pretreated material or exogenously added. Saccharification is generally performed in stirred-tank reactors or fermentors under controlled pH, temperature, and mixing conditions. A saccharification step may last up to 200 hours. Saccharification may be carried out at temperatures from about 30.degree.C. to about 65.degree.C., in particular around 50.degree.C., and at a pH in the range of between about 4 and about 5, in particular, around pH 4.5. Saccharification can be performed on the whole pretreated material.

Fermentation.

In the fermentation step, sugars, released from the lignocellulose as a result of the pretreatment and enzymatic hydrolysis steps, are fermented to one or more organic substances, e.g., ethanol, by a fermenting microorganism, such as yeasts and/or bacteria. The fermentation can also be carried out simultaneously with the enzymatic hydrolysis in the same vessels, again under controlled pH, temperature and mixing conditions. When saccharification and fermentation are performed simultaneously in the same vessel, the process is generally termed simultaneous saccharification and fermentation or SSF.

Fermenting microorganisms and methods for their use in ethanol production are known in the art (Sheehan, "The road to Bioethanol: A strategic Perspective of the US Department of Energy's National Ethanol Program" In: "Glucosyl Hydrolases For Biomass Conversion", ACS Symposium Series 769, 2001, American Chemical Society; Washington, D.C.). Existing ethanol production methods that utilize corn grain as the biomass typically involve the use of yeast, particularly strains of *Saccharomyces cerevisiae*. Such strains can be utilized in the methods of the invention. While such strains may be preferred for the production of ethanol from glucose that is derived from the degradation of cellulose and/or starch, the methods of the present invention do not depend on the use of a particular microorganism, or of a strain thereof, or of any particular combination of said microorganisms and said strains.

Yeast or other microorganisms are typically added to the hydrolysate and the fermentation is allowed to proceed for 24-96 hours, such as 35-60 hours. The temperature of fermentation is typically between 26-40.degree.C., such as 32.degree.C., and at a pH between 3 and 6, such as about pH 4-5.

A fermentation stimulator may be used to further improve the fermentation process, in particular, the performance of the fermenting microorganism, such as, rate enhancement and ethanol yield. Fermentation stimulators for growth include vitamins and minerals. Examples of vitamins include multivitamin, biotin, pantothenate, nicotinic acid, meso-inositol, thiamine, pyridoxine, para-aminobenzoic acid, folic acid, riboflavin, and vitamins A, B, C, D, and E (Alfenore et al., "Improving ethanol production and viability of *Saccharomyces cerevisiae* by a vitamin feeding strategy during fed-batch process", 2002, Springer-Verlag). Examples of minerals include minerals and mineral salts that can supply nutrients comprising phosphate, potassium, manganese, sulfur, calcium, iron, zinc, magnesium and copper.

Recovery.

Following fermentation (or SSF), the mash is distilled to extract the ethanol. Ethanol with a purity greater than 96 vol. % can be obtained.

Combined Starch Hydrolysis and Cellulolytic Material Hydrolysis.

The transgenic plants and plant parts disclosed herein can be used in methods involving combined hydrolysis of starch and of cellulosic material for increased ethanol yields. In addition to providing enhanced yields of ethanol, these methods can be performed in existing starch-based ethanol processing facilities.

Starch is a glucose polymer that is easily hydrolyzed to individual glucose molecules for fermentation. Starch hydrolysis may be performed in the presence of an amylolytic microorganism or enzymes such as amylase enzymes. In certain embodiments of the invention, starch hydrolysis is performed in the presence of at least one amylase enzyme. Examples of suitable amylase enzymes include alpha-amylase (which randomly cleaves the alpha(1-4)glycosidic linkages of amylose to yield dextrin, maltose or glucose molecules) and glucoamylase (which cleaves the .alpha.(1-4) and .alpha.(1-6)glycosidic linkages of amylose and amylopectin to yield glucose).

In the inventive methods, hydrolysis of starch and hydrolysis of cellulosic material can be performed simultaneously (i.e., at the same time) under identical conditions (e.g., under conditions commonly used for starch hydrolysis). Alternatively, the hydrolytic reactions can be performed sequentially (e.g., hydrolysis of lignocellulose can be performed prior to hydrolysis of starch). When starch and cellulosic material are hydrolyzed simultaneously, the conditions are preferably selected to promote starch degradation and to activate lignocellulolytic enzyme(s) for the degradation of lignocellulose. Factors that can be varied to optimize such conditions include physical processing of the plants or plant parts, and reaction conditions such as pH, temperature, viscosity, processing times, and addition of amylase enzymes for starch hydrolysis.

The methods may use transgenic plants (or plant parts) alone or a mixture of non-transgenic plants (or plant parts) and plants (or plant parts) transformed according to the present invention. Suitable plants include any plants that can be employed in starch-based ethanol production (e.g., corn, wheat, potato, cassaya, etc). For example, the present inventive methods may be used to increase ethanol yields from corn grains.

The plants of the invention find use in biomass conversion methods for producing sugars or biofuels from plant biomass. Herein, the term "biofuels" refers to any fuel derived from harvested plant parts. Biofuels comprise but are not limited to biodiesel, vegetable oils, bioalcohols (i.e. ethanol, methanol, propanol, butanol, etc.) and biogases (i.e. methane). The plants of the invention are engineered to accumulate higher concentrations of starch in their green tissues thus providing a rich source of carbohydrates which then can be converted to biofuels. Herein, the term "free sugars" defines any carbohydrate derived from plant biomass that can be further processed to make fermentable sugars, chemicals, biofuels, plastics, feed additives or any other commercially important product. One embodiment of the current application provides a method of improving the yield of free sugars from plant biomass comprising manipulating a plant to down-regulate the activity of one or more starch degradation enzymes. The resultant plant will contain increased levels of starch which then can be converted to free sugars in a conventional biomass conversion method. Herein, the term "biomass conversion method" defines any process that converts plant parts into fermentable sugars, biofuels, chemicals, plastics, feed additives, or any other commercially important products. Biomass conversion methods may also contain a subcategory herein referred to as a "non-animal feed biomass conversion method". Non-animal feed biomass conversion method defines any process that converts plant parts into fermentable sugars, biofuels, chemicals and plastics not destined for animal consumption.

The compositions and methods of the invention are useful in the production of dextrose for fructose syrups, specialty sugars, and in alcohol and other end-product (e.g. organic acid, ascorbic acid, and amino acids) production from fermentation of starch (G. M. A van Beynum et al., Eds. (1985) *Starch Conversion Technology*, Marcel Dekker Inc. NY). Production of alcohol from the fermentation of starch derived from the green tissues of the plants of the invention may include the production of fuel alcohol or potable alcohol.

In certain preferred embodiments, the alcohol will be ethanol. In particular, alcohol fermentation production processes are characterized as wet milling or dry milling processes. In some embodiments, the plants are subjected to a wet milling fermentation process and, in other embodiments, a dry milling process is used. In certain embodiments, ethanol may be produced using a raw starch hydrolysis method.

Dry grain milling involves a number of basic steps, which generally include: grinding, cooking, liquefaction, saccharification, fermentation and separation of liquid and solids to produce alcohol and other co-products. Plant material and particularly whole cereal grains, such as maize, wheat or rye are ground. In some cases the grain may be first fractionated into component parts. The ground plant material may be milled to obtain a coarse or fine particle. The ground plant material is mixed with liquid in a slurry tank. The slurry is subjected to high temperatures in a jet cooker along with liquefying enzymes (e.g. alpha amylases) to solubles and hydrolyze the starch in the cereal to dextrins. The mixture is cooled down and further treated with saccharifying enzymes to produce glucose. The mash containing glucose is then fermented for approximately 24 to 120 hours in the presence of fermentation microorganisms, such as ethanol producing microorganism and particularly yeast (*Saccharomyces* spp). The solids in the mash are separated from the liquid phase and alcohol such as ethanol and useful co-products such as distillers' grains are obtained.

In some embodiments, the saccharification step and fermentation step are combined and the process is referred to as simultaneous saccharification and fermentation or simultaneous saccharification, yeast propagation and fermentation.

In other embodiments, the cooking step or exposure of the green starch containing substrate to temperatures above the gelatinization temperate of the starch in the substrate may be eliminated. These fermentation processes in some embodiments include milling of a cereal grain or fractionated grain and combining the ground cereal grain with liquid to form a slurry, which is then mixed in a single vessel with amylases, glucoamylases, and/or other enzymes having granular starch hydrolyzing activity and yeast to produce ethanol and other co-products (U.S. Pat. No. 4,514,496, WO 04/081193 and WO 04/080923). In some embodiments, the enzymes useful for fermentation process include alpha amylases, proteases, pullulanases, isoamylases, cellulases, hemicellulases, xylanases, cyclodextrin glycotransferases, lipases, phytases, laccases, oxidases, esterases, cutinases, granular starch hydrolyzing enzyme and other glucoamylases.

In some embodiments the invention is directed to a sugarcane containing high amounts of starch in its' green tissues. A sugarcane plant containing high starch may be desirable in conventional operations that employ cane sugar in a fermentation-distillation operation which may also utilize a high starch bagasse by-product as a high valued fuel source.

In another embodiment, the invention is directed to a transformed plant, the genome of which is augmented with a recombinant polynucleotide encoding at least one processing enzyme operably linked to a promoter sequence, the sequence of which polynucleotide is optimized for expression in the plant. It may be beneficial to create a plant with increased green starch that has been further modified to express a processing enzyme that when activated will be capable of self-processing the substrate upon which it acts to obtain the desired result as described in, US20030135885 and US7102057 herein incorporated by reference. In accordance with the present invention, a "self-processing" plant or plant part has incorporated therein an isolated polynucleotide encoding a processing enzyme capable of processing, e.g., modifying, starches, polysaccharides, lipids, proteins, and the like in plants, wherein the processing enzyme can be mesophilic, thermophilic or hyperthermophilic, and may be activated by grinding, addition of water, heating, or otherwise providing favorable conditions for function of the enzyme. The isolated polynucleotide encoding the processing enzyme is integrated into a plant or plant part for expression therein. Upon expression and activation of the processing enzyme, the plant or plant part of the present invention processes the substrate upon which the processing enzyme acts. Therefore, the plant or plant parts of the present invention are capable of self-processing the substrate of the enzyme upon activation of the processing enzyme contained therein in the absence of or with reduced external sources normally required for processing these substrates. As such, the transformed plants, transformed plant cells, and transformed plant parts have "built-in" processing capabilities to process desired substrates via the enzymes incorporated therein according to this invention. Preferably, the processing enzyme-encoding polynucleotide are "genetically stable," i.e., the polynucleotide is stably maintained in the transformed plant or plant parts of the present invention and stably inherited by progeny through successive generations.

In accordance with the present invention, methods which employ such plants and plant parts can eliminate the need to mill or otherwise physically disrupt the integrity of plant parts prior to recovery of starch-derived products. For example, the invention provides improved methods for processing maize and other grain to recover starch-derived products. The invention also provides a method which allows for the recovery of starch granules that contain levels of starch degrading enzymes, in or on the granules that are adequate for the hydrolysis of specific bonds within the starch without the requirement for adding exogenously produced starch hydrolyzing enzymes. The invention also provides improved products from the self-processing plant or plant parts obtained by the methods of the invention.

In addition, the "self-processing" transformed plant part, e.g., grain, and transformed plant avoid major problems with existing technology, i.e., processing enzymes are typically produced by fermentation of microbes, which requires isolating the enzymes from the culture supernatants, which costs money; the isolated enzyme needs to be formulated for the particular application, and processes and machinery for adding, mixing and reacting the enzyme with its substrate must be developed. The transformed plant of the invention or a part thereof is also a source of the processing enzyme itself as well as substrates and products of that enzyme, such as sugars, amino acids, fatty acids and starch and non-starch polysaccharides. The plant of the invention may also be employed to prepare progeny plants such as hybrids and inbreds.

The plant may be a monocot, such as maize, or a dicot. Preferably, the plant is a energy crop or a commercially grown plant. Herein the term "processing enzyme" is selected from the group consisting of an α-amylase, glucoamylase, glucose isomerase, glucanase, β-amylase, α-glucosidase, isoamylase, pullulanase, neo-pullulanase, iso-pullulanase, amylopullulanase, cellulase, exo-1,4-β-cellobiohydrolase, exo-1,3-β-D-glucanase, β-glucosidase, endoglucanase, L-arabinase, α-arabinosidase, galactanase, galactosidase, mannanase, mannosidase, xylanase, xylosidase, protease, glucanase, esterase, phytase, and lipase. Preferably, the processing enzyme is a starch-processing enzyme selected from the group consisting of α-amylase, glucoamylase, glucose isomerase, β-amylase, α-glucosidase, isoamylase, pullulanase, neo-pullulanase, iso-pullulanase, and amylopullulanase. More preferably, the enzyme is selected from α-amylase, glucoamylase, glucose isomerase, glucose isomerase, α-glucosidase, and pullulanase. The processing enzyme is further preferably hyperthermophilic. In accordance with this aspect of the invention, the enzyme may be a non-starch degrading enzyme selected from the group consisting of protease, glucanase, xylanase, esterase, phytase, and lipase. Such enzymes may further be hyperthermophilic. In a preferred embodiment, the enzyme accumulates in the vacuole, endoplasmic reticulum, chloroplast, starch granule, seed or cell wall of a plant. Moreover, in another embodiment, the genome of plant may be further augmented with a second recombinant polynucleotide comprising a non-hyperthermophilic enzyme.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

EXAMPLES

The invention will be further described by the following examples, which are not intended to limit the scope of the invention in any manner.

Example 1

Generation of Transgenic Maize Plants

The *Zea mays* cDNA sequences for α-amylase (Genbank Accession L25805), β-amylase (Genbank Accession Z25871) and α-glucan water dikinase (R1, Genbank Accession CD973834) were obtained from NCBI. RNAi fragments (495 bp of α-amylase, SEQ ID NO: 1; 500 bp of α-amylase, SEQ ID NO: 2; and 330 bp of R1, SEQ ID NO: 3) from the 3'-ends of the coding regions of these genes were synthesized by Geneart (Geneart AG). During synthesis, attB1 and attB2 sites were added to 5' and 3'-ends of these three coding sequence fragments, respectively. All three RNAi fragments were recombined into pDONR221 using the BP Reaction from Gateway® Cloning Technology (Invitrogen Life Science).

Destination vector 15912 is a binary vector containing a phosphomannose isomerase (PMI) gene that allows selection of transgenic cells with mannose. Vector 15912 also provides a method for making an RNAi cassette using Gateway® Cloning Technology (Invitrogen Life Science). In 15912, the RNAi cassette is expressed in green tissues (leaf and stem) using the promoter from the maize gene encoding phosphoenol carboxylase (PEPC; Hudspeth & Grula. (1989) Plant Mol. Biol. 12: 579-589).

The Gateway Entry RNAi fragments (SEQ ID #s 1, 2 and 3) created by Geneart were recombined into vector 15912 using the LR Reaction (Gateway® LR Clonase® Enzyme Mix, Invitrogen), creating binary vectors expressing RNAi cassettes for α-amylase (17306), βamylase (17307) and R1 (17308). Binary vectors were verified by restriction digest and sequencing. Clones used to transform maize plants are demonstrated in Table 1.

Transformation of immature maize embryos is performed essentially as described in Negrotto et al., Plant Cell Reports 19:798-803 (2000). Various media constituents described therein can be substituted.

*Agrobacterium* strain LBA4404 (Invitrogen) containing the plant transformation plasmid is grown on YEP (yeast extract (5 g/L), peptone (10 g/L), NaCl (5 g/L), 15 g/l agar, pH 6.8) solid medium for 2 to 4 days at 28° C. Approximately $0.8 \times 10^9$ *Agrobacteria* are suspended in LS-inf media supplemented with 100 μM acetosyringone (As) (LSAs medium) (Negrotto et al., Plant Cell Rep 19:798-803 (2000)). Bacteria are pre-induced in this medium for 30-60 minutes.

Immature embryos from maize line, A188, or other suitable maize genotypes are excised from 8-12 day old ears into liquid LS-inf+100 μM As (LSAs). Embryos are vortexed for 5 seconds and rinsed once with fresh infection medium. Infection media is removed and *Agrobacterium* solution is then added and embryos are vortexed for 30 seconds and allowed to settle with the bacteria for 5 minutes. The embryos are then transferred scutellum side up to LSAs medium and cultured in the dark for two to three days. Subsequently, between 20 and 25 embryos per petri plate are transferred to LSDc medium supplemented with cefotaxime (250 mg/l) and silver nitrate (1.6 mg/l) (Negrotto et al., Plant Cell Rep 19:798-803 (2000)) and cultured in the dark for 28° C. for 10 days.

Immature embryos producing embryogenic callus are transferred to LSD1M0.5S medium (LSDc with 0.5 mg/l 2,4-D instead of Dicamba, 10 g/l mannose, 5 g/l sucrose and no silver nitrate). The cultures are selected on this medium for 6 weeks with a subculture step at 3 weeks. Surviving calli are transferred either to LSD1M0.5S medium to be bulked-up or to Reg1 medium (as described in Negrotto et al., Plant Cell Rep 19:798-803 (2000). Following culturing in the light (16 hour light/8 hour dark regiment), green tissues are then transferred to Reg2 medium without growth regulators (as described in Negrotto et al., Plant Cell Rep 19:798-803 (2000) and incubated for 1-2 weeks. Plantlets are transferred to Magenta GA-7 boxes (Magenta Corp, Chicago Ill.) containing Reg3 medium (as described in Negrotto et al. 2000) and grown in the light. Plants that were PCR positive for PMI and iOsSH1i1-01 (loop) and negative for Spectinomycin were transferred to soil and grown in the greenhouse. A total of 148 $T^0$ plants were grown to maturity (Table 2). And the plant samples of selected events were collected for Lugol's staining, starch analysis, fermentation and storage stability studies.

TABLE 1

Green Starch Constructs

| Construct | Expression Cassette (promoter & gene) |
|---|---|
| 17306 | PePC promoter + alpha-amylase |
| 11307 | PePC promoter + beta-amylase |
| 17308 | PePC promoter + R1 |

TABLE 2

Number of $T^0$ events carried forward to the greenhouse to maturity.

| Construct # | Number or $T^0$ transferred to Greenhouse |
|---|---|
| 17306 | 38 (21L + 17M) |
| 17307 | 38 (33L + 5M) |
| 17308 | 35 (24L + 11M) |

*Taqman® PCR copy number, L—low copy, M—Medium copy

Example 2

Sample Collection and Prescreening of Transgenic Maize Events

Leaf samples were taken in the morning from mature T0 maize plants 1-3 days before pollination. Leaf samples were collected for starch analysis above and below the pollinated ear. Samples were bagged separately and labeled by plant ID, kept at 4° C. until further analyzed. Herein, the following leaf samples are referred to as "mature".

Stem samples were collected in the morning from mature T0 maize plants at about 20 days post-pollination. The tassel was removed after pollination. Plants were placed in a dark room overnight prior to collection. Stem tissue below the tassel that was more than two leaves above the cob was collected. Samples were bagged separately and kept in the dark at 4° C. until further analyzed.

Leaf samples were also collected directly from young $T^0$ maize plant seedlings directly from tissue culture and prior to being grown in soil. Herein, these samples are referred to as "seedlings"

Prescreening of starch accumulation in $T^0$ maize events was carried out using Lugol's staining solution. Lugol's solution selectively stains starch dark blue to black, and can be observed visually under a microscope. The degree of staining relative to null controls allowed for the fast visual preselection of events with increased starch in green tissues to be carried forward for starch analysis and fermentation experiments.

Prescreening of event leaf tissue was carried out by collecting four leaf punches in homogeneous section of the leaf near the tip. Two leaf punches were placed into each well (two wells per sample) of a 96-well block. The wells were filled with 95% ethanol, covered and refrigerated at 4° C. overnight to extract chlorophyll. Ethanol was removed the next day with a disposable pipette. Next, 150 µl of 5% Lugol's Iodine was added to each well. The block was then vacuum infiltrated for 20 minutes at 25-27 psi to evenly stain all samples. The Lugol's solution was removed and samples were washed with water several times to destain as much as possible. The stained samples were placed on a microscope slide including a control for comparison. Next, the stained samples were viewed under microscope and assigned a numerical value (1-5, where 1=low starch accumulation, 5=high starch accumulation) based on stain intensity which reflected the starch content/accumulation; and recorded photographically. Relative Lugol staining scores are outlined in Tables 3-5. Visual scores were used to determine which events to carry out further starch analysis and fermentation experiments. It was found in the lab that the degree of starch accumulation in stem tissue of maize plants as indicated by starch staining, is comparative to the degree of starch staining in corresponding leaf tissue from the same plant. It was also found that in the case of down-regulated beta-amylase under control of a PePC promoter, starch accumulates at a higher degree in young maize green tissue versus mature maize green tissue (See Table 4). A third sample was therefore collected from young leaf sample taken from mature plants grown in the greenhouse.

TABLE 3

Construct 17306 Leaf Starch Staining
(PePC promoter + alpha-amylase RNAi)

| Plant ID | Seedling Rating | Mature Rating (2 Scores) |
|---|---|---|
| CONTROL 1 | | |
| CONTROL 2 | | |
| MZBF080329A001A | N/A | 1 + 1 |
| MZBF080329A002A | 5 | 2 + 1 |
| MZBF080329A005A | 5 | 4 + 4 |
| MZBF080329A007A | 3 | 2 + 1 |
| MZBF080329A008A | 3 | 5 + 4 |
| MZBF080329A022A | 4 | 4 + 3 |
| MZBF080329A025A | 5 | 4 + 4 |
| MZBF080329A031A | 5 | 4 + 4 |
| MZBF080329B004A | 5 | 4 + 4 |
| MZBF080329B009A | 5 | 4 + 5 |
| MZBF080329B020A | 5 | 4 + 3 |
| MZBF080329B025A | 4 | 2 + 1 |
| MZBF080329B034A | 5 | 2 + 2 |
| MZBF080329B039A | 5 | 4 + 4 |
| MZBF080329B041A | N/A | 4 + 4 |

TABLE 4

Construct 17307 Leaf Starch Staining
(PePC promoter + beta-amylase RNAi)

| Plant ID | Seedling Rating | Mature Rating | Mature young leaf |
|---|---|---|---|
| CONTROL 1 | | | |
| CONTROL 2 | | | |
| MZBF080325A012A | 4 | 2 | |
| MZBF080325A013A | 2 | | |
| MZBF080325A015A | 2 | | |
| MZBF080325A019A | 4 | 2 | |
| MZBF080325A041A | 4 | | |
| MZBF080325A044A | 4 | 1 | |
| MZBF080325A047A | 4 | | |
| MZBF080325A050A | 4 | 1 | 3 |
| MZBF080325A063A | 4 | 2 | |
| MZBF080325A066A | 4 | | |
| MZBF080325A076A | 4 | 2 | 5 |
| MZBF080325A085A | 4 | 2 | 4 |
| MZBF080325A093A | 4 | 3 | |
| MZBF080325A104A | 5 | 2 | 5 |
| MZBF080325A115A | 4 | | |
| MZBF080325A123A | 4 | 1 | |
| MZBF080325A136A | 4 | 2 | |
| MZBF080325A139A | 2 | 2 | |

TABLE 5

Construct 17308 Leaf Starch Staining
(PePC promoter + glucan water dikinase RNAi)

| Plant ID | Seedling Rating | Mature Rating |
|---|---|---|
| CONTROL 1 | | |
| CONTROL 2 | | |
| MZBF080320A001A | 5 | 5 |
| MZBF080320A004A | 2 | |
| MZBF080320A008A | 4 | |
| MZBF080320A010A | 4 | |
| MZBF080320A013A | 5 | 4 |
| MZBF080320A015A | 5 | 4 |
| MZBF080320A026A | 1 | 2 |
| MZBF080320A029A | 5 | 4 |
| MZBF080320A034A | 4 | 4 |
| MZBF080320A036A | 5 | 5 |
| MZBF080320A041A | 4 | |
| MZBF080320A043A | 4 | |
| MZBF080320A053A | 4 | |
| MZBF080320A055A | 4 | |
| MZBF080320A059A | 5 | 5 |
| MZBF080320A061A | 5 | 5 |
| MZBF080320A062A | 2 | |
| MZBF080320A068A | 2 | |
| MZBF080320A069A | 5 | 4 |
| MZBF080320B004A | 2 | |
| MZBF080320B006A | 4 | |

Example 3

Starch Estimation in Lyophilized Maize Plant Tissue Samples

Collected stem and leaf tissue was lyophilized and ground to fine powder. Samples were then weighed (~100 mg per sample) in labeled 15 mL centrifuge tubes. To dissolve out soluble sugar from the samples, 2 mL of 80% ethanol was added to each sample and vortexed to mix thoroughly. Samples were then centrifuged for 5 minutes at 3,000 rpm and the supernatant was carefully pipetted out and discarded. Next, 2 mL of cold water (4° C.) was added to each sample tube and vortexed to mix thoroughly. Samples were then centrifuged for 5 minutes at 3,000 rpm and the supernatant was carefully pipetted out and discarded. Following centrifugation, 3 mL of α-amylase (300 U), (Megazyme's Total starch Assay Kit—AOAC Method 996.11) in MOPS buffer (50 mM, pH 7.0) was added to each sample tube and stirred vigorously to ensure no clumping of the sample at the bottom of the tube. Samples were incubated in a 100° C. water bath for 6 min. During incubation, the samples were vortexed at 2, 4 and 6 minutes to avoid clumping of sample. After incubation the samples were transferred to a 50° C. water bath after 6 minutes. Next, 4 mL of NaOAc buffer (200 mM NaOAc, pH 4.5) and 0.1 mL of amyloglucosidase (20 U) (Megazyme's Total starch Assay Kit—AOAC Method 996.11) was added, and the tubes were vortexed and incubated for another 30 minutes at 50° C. After 30 minutes of incubation, the volume of each tube was brought to 10 mL with Milli-Q water, and the tubes were vortexed and centrifuged for 10 minutes at 3,000 rpm. Following centrifugation, 2 mL of the supernatants were added in duplicate to labeled glass tubes. Also, 1.9 mL water and 0.1 mL D-glucose standard (1 mg/mL), and 2 mL of water were added in duplicate to labeled glass test tubes to serve as the standard and the blank, respectively. Next, 3 mL of GOPOD reagent (containing >12000 U Glucose Oxidase, >650 U Peroxidase & 4-aminoantipyrine 80 mg in 1 liter water) was added to each tube (including the D-glucose controls and reagent b1nks), and the tubes were vortexed and incubated for 20 minutes in a 50° C. water bath. Following incubation, 300 μL from each tube was transferred to a 96 well plate and the OD was taken at 510 nm. Observed OD (over reagent blank) for each sample compared to that for D-glucose control was used calculate the amount free glucose released by the hydrolytic reaction catalyzed by amylase and amyloglucosidase from the starch present in each sample.

Estimated free glucose was converted to the amount of starch in fresh and dry weight of the tissue samples using an adjustment factor of 162/180. Starch estimation in lyophilized maize plant leaf and stem tissue samples are demonstrated in Tables 6-7.

TABLE 6

Leaf starch analysis of 17307 and 17308 transgenic maize lines

| Sample | Plant ID | Starch per leaf (ug/g) | Average Starch per leaf (ug/g) |
|---|---|---|---|
| Controls | control-1 | 633.44 | 623 |
|  | control-2 | 613.24 |  |
| 17307 (prPePC + Beta-amylase RNAi) | A044A | 433.43 | 422 |
|  | A063A | 410.53 |  |
|  | A104A | 451.74 |  |
|  | A115A | 393.49 |  |
| 17308 (prPePC + R1-GWD RNAi) | A013A | 1558.89 | 1261 |
|  | A016A | 577.99 |  |
|  | A036A | 1411.91 |  |
|  | A059A | 1494.99 |  |

TABLE 7

Stem starch analysis of 17307 and 17308 transgenic maize lines

| Sample | Plant ID | Starch per stem (ug/g) | Average Starch per stem (ug/g) |
|---|---|---|---|
| Controls | C1 | 1425.2 | 1200 |
|  | C2 | 975.5 |  |
| 17307 (prPePC + Beta-amylase RNAi) | A076A | 2813.1 | 2767 |
|  | A085A | 2690.6 |  |
|  | A104A | 2797.0 |  |
| 17308 (prPePC + R1-GWD RNAi) | A013A | 2506.1 | 2648 |
|  | A015A | 2709.1 |  |
|  | A036A | 2728.4 |  |

Example 4

Leaf and Stem Biomass Fermentation of Maize Plant Tissue Samples

Two grams of leaf tissue from each event including wild type tissues were lyophilized for 18 hours and the moisture content was mass balanced. The lyophilized tissues were powdered by two 30 seconds vibration cycles using a Kleco machine (Garcia Manufacturing, Visalia, Calif., Model no. KLECO 8200). For comparison, a hot water treatment (Dry Grind (DG) Process) and a low temperature treatment (Raw Starch (RS) Process) were performed to determine effects on EtOH yield. Air dried leaf tissues (about one month old) were used to carry out fermentation experiments and sample preparation was followed as described above.

Fermentations using leaf biomass were initiated using 150 mg of the dry powder subjected to 3 ml volume of fermentation solution (1% YE, 2% Peptone, 0.05M citrate buffer, pH 4.8, 2.5 ug/mL Tet, 80 uL of 5× diluted yeast slurry from EtOH Technology), which is equivalent to a 5% solid loading. For low temperature raw starch fermentations, fermentations were conducted at 30° C. including two replicates for each event. Next, 20 uL of Sigma glucoamylase (Sigma A7095-50 mL) was added to the fermentation reaction in order to hydrolyze starch. Fermentations were carried out in 15 mL falcon tubes using a stir bar to mix the samples during the process. A 100 uL aliquot was taken for each sample at 0, 17, 24, and 48 hour time points and analyzed by HPLC for EtOH content.

Quantitative HPLC analysis of EtOH content for each leaf sample was carried out. First, sample aliquots from the fermentation were filtered using a 0.4 μm filter for 8 minutes at 8000 rpm. EtOH was separated through a Micro-Guard Cation-H Refill Cartridges 30×4.6 mm (Bio-Rad, Cat no. 125-0119) and Aminex HPX-87H Ion Exclusion Column 300×7.8 mm (Bio-Rad, Cat no. 125-0140) and detected with a R1 detector using High Performance Liquid Chromatography (HPLC, Waters Alliance). The analysis of variance (ANOVA) was carried out with the 17 hour time point data. The comparison was done between the wild type treated with GA and the transgenic line samples. When the ANOVA resulted in P value at least less than 0.05 or 0.01, it has been labeled with "*" or "**" indicating significant difference at 95% or 99% confidence level respectfully. Biomass fermentation data from leaf samples is demonstrated in Table 8.

Hot water treatment (DG) process and low temperature treatment (RS) treatments were compared based on EtOH yield. Hot water treatment was carried out essentially as described in the RS process. First, 150 mg of powdered tissue from air-dried leaf was mixed with 2 mL of water and incubated in the hot water bath at 85 C for 1 hour for DG process while it was left at room temperature for 1 hour for RS process prior to fermentation. After the high temperature treatment, 1 mL of fermentation solution was added to each pretreated samples as described for the RS treatment, resulting in a 5% solid loading. Fermentation was then carried out as described above for the RS procedure. HPLC analysis of EtOH yield was same as described above. ANOVA was carried out in the same way, and the grouping of events with corresponding level of EtOH yields was differentiated with superscripts (a, b, and c), and different superscripts indicate significant difference between groups at least 95% confidence level. The comparison of the hot water treatment (DG) process and low temperature treatment (RS) process from leaf samples is demonstrated in Table 9.

Stem biomass fermentation can be carried out essentially as described in the methods above for leaf biomass fermentations. One difference noted in the prescreening visual data is that down-regulation of alpha-amylase, beta-amylase, or glucan water dikinase all led to starch accumulation within the green peripheral vascular tissue (containing chloroplast) and very little to none in the central vascular portion (containing no chloroplast) of the stem, as expected. Therefore, to experimentally demonstrate an increase in EtOH yield by using stem biomass, the central vascular bundle would need to be extracted and only the stem peripheral vascular tissue fermented. The following process can be used to measure EtOH yield in the fermentation of stem biomass. First, central vascular tissue will be removed from stem samples and the two grams of the remaining peripheral vascular tissue will be lyophilized for 18 hrs, moisture content mass balanced and the sample pulverized to powder as described for leaf tissue. Next, 150 mg of the dry powder subjected to 3 ml volume of fermentation solution (1% YE, 2% Peptone, 0.05M citrate buffer, pH 4.8, 2.5 ug/mL Tet, 80 uL of 5× diluted yeast slurry from EtOH Technology), which is equivalent to a 5% solid loading. Fermentation will be conducted at 30° C. including two replicates for each event. Next, 20 uL of Sigma glucoamylase (Sigma A7095-50 mL) will be added to the fermentation reaction in order to hydrolyze starch. Fermentations will be carried out in 15 mL falcon tubes using a stir bar to mix samples. Sampling of 100 uL aliquot will be taken at 0, 17, 24, and 48 hour time points for HPLC analysis.

TABLE 8

EtOH yields from leaf tissues of different transgenic lines. Values indicate % EtOH from each fermentation initiated with a 5% solid loading. Data labeled * or ** indicates significant difference at 95% or 99% confidence level, respectively when compared to the wild type treated with Sigma GA (Sigma A7095-50 mL). Wt-Enz indicates that the fermentation was conducted with starch hydrolysis enzymes.

| Events | Lines 17306 | Events | Lines 17307 | Events | Lines 17308 |
|---|---|---|---|---|---|
| Wt-Enz | 0.188 | Wt-Enz | 0.188 | Wt-Enz | 0.188 |
| MZBF080329A007A | 0.195 | MZBF080325A044A | 0.162 | MZBF080320A013A | 0.746** |
| MZBF080329A008A | 0.196 | MZBF080325A063A | 0.117 | MZBF080320A016A | 0.299** |
| MZBF080329A025A | 0.221 | MZBF080325A104A | 0.234** | MZBF080320A036A | 0.611** |
| MZBF080329A031A | 0.209 | MZBF080325A115A | 0.170 | MZBF080320A059A | 0.483** |
| MZBF080329B004A | 0.230 | | | | |

TABLE 9

Comparison of hot water treatment (Dry Grind Process) and low temperature treatment (Raw Starch Process) on EtOH yield from leaf tissue with increased starch content.

| Line | Event | Temperature | EtOH, % |
|---|---|---|---|
| 17306 | MZBF080329B025A | Low (RT) | 0.186 |
| | | High (85 C.) | 0.176 |

Example 5

Storage Stability of Dried Maize Green Tissue

The leaf located in proximity of the maize ear was sampled 11-12 weeks after planting for each event. The mid-vein was then stripped off from the middle of the leaf. The right side of the leaf was freeze dried and frozen at −80° C. and the left side of the leaf was placed on the lab bench and air dried under a fan for 55 hours. The air dried and frozen leaf samples were then lyophilized for 60 hours. The lyophilized tissues were then powdered by two 30 second vibration cycles using a Kleco (Garcia Manufacturing, Visalia, Calif., Model no. KLECO 8200). The leaf material from both air dried and freeze dried samples were then analyzed for starch content to compare if the starch was stable under air dried storage condition in the leaf. Starch from dried tissues was analyzed as described in Example 3. Dried leaf storage stability data is described in Table 10.

TABLE 10

Starch accumulation measured (μg/mg) in dried leaf tissue relative to wild type controls.

| | | Amount of Starch in Dried Leaf Tissue | |
|---|---|---|---|
| Plant ID | Samples | ug/mg of dry leaf | Average ug/mg of dry leaf |
| Control | C-1 | −210.1 | 0 |
| | C-2 | −429.4 | |
| | C-3 | −170.8 | |
| | C-4 | −120.8 | |
| 17306 | A008A | 593.7 | 0 |
| | A025A | −1319.3 | |
| | B004A | −498.8 | |
| | B041A | −4979.6 | |
| 17307 | A041A | 50.6 | 0 |
| | A044A | −2058.2 | |
| | A066A | −359.7 | |
| | A072A | −5008.1 | |

TABLE 10-continued

Starch accumulation measured (μg/mg) in dried leaf tissue relative to wild type controls.

| | | Amount of Starch in Dried Leaf Tissue | |
|---|---|---|---|
| Plant ID | Samples | ug/mg of dry leaf | Average ug/mg of dry leaf |
| 17308 | A008A | −381.9 | 229 |
| | A010A | 453.4 | |
| | A055A | 347.5 | |
| | A060A | −119.7 | |
| | B006A | 408.1 | |
| | B012A | 663.9 | |

Example 6

Down-Regulation of Starch Degradation Enzymes in Sugarcane

The *Zea mays* cDNA sequences for α-amylase (Genbank Accession L25805), β-amylase (Genbank Accession Z25871) and α-glucan water dikinase (R1, Genbank Accession CD973834) were obtained from NCBI. These sequences were used to BLAST against the DFCI Sugarcane Gene Index Database. Homologs aligning at 82%, 45% and 90% were identified. RNAi fragments of about 200-400 bp can be synthesized from the sugarcane homologues to suppress or inhibit α-amylase, β-amylase and R1 in sugarcane essentially as was carried out in maize. Methods for down-regulation of genes in sugarcane have been demonstrated in Groenewal et al (2006) Transgenic Res. herein incorporated by reference. Sugarcane RNAi fragments will be synthesized by Geneart (Geneart AG). During synthesis, attB1 and attB2 sites will be added to 5' and 3'-ends of these three coding sequence fragments, respectively. All three RNAi fragments will be recombined into pDONR221 using the BP Reaction from Gateway® Cloning Technology (Invitrogen Life Science). Destination vector 15912 is a binary vector with a phosphomannose isomerase (PMI) gene that allows selection of transgenic cells with mannose. It has been shown that sugarcane can be transformed and selected by PMI in Mukesh et al. Plant Cell Rep (2007) 26:581-590 herein incorporated by reference. This vector also provides a method for making an RNAi cassette using Gateway® Cloning Technology (Invitrogen Life Science). The RNAi cassettes can be driven by a number of promoters that show expression in green tissues. In 15912 the RNAi cassette is expressed in green tissues (leaf and stem) using the promoter from the maize gene encoding phosphoenolpyruvate carboxylase (PEPC; Hudspeth & Grula. (1989) Plant Mol. Biol. 12: 579-589). A phosphoenolpyruvate carboxylase has been identified in sugarcane by Henrick et al. Plant Molecular Biology (1992) 20:663-671 herein incorporated by reference. Also, the use of a PEPC promoter to drive expression of gene cassettes in sugarcane has been described by Barga et al (2003) The Journal of New Seed herein incorporated by reference.

Gateway Entry vectors created by Geneart may be recombined into 15912 using the LR Reaction (Gateway® LR Clonase® Enzyme Mix, Invitrogen), creating binary vectors expressing RNAi cassettes for α-amylase, β-amylase and R1. Binary vectors will be verified by restriction digest and sequencing.

Sugarcane transformation may be achieved by micro projectile bombardment or *agrobacterium* mediated transformation.

Microprojectile transformation is achieved by coprecipitating in a one to one ratio 1-5 µg of gel purified polynucleotide coding for a selectable marker and polynucleotide coding for a plant based expression construct containing the RNAi of interest as well as appropriate regulatory elements, onto tungsten or gold particles. The coated particles are used to bombard embryogenic sugarcane callus and thus transfer the polynucleotide sequences into the nucleus of the callus cells. Transgenic calli can be selected based upon the activity of the selectable marker chosen. One of skill in the art would be able to determine an appropriate selectable marker for sugarcane transformation. In addition, there is a wide variety of promoters, enhancers, targeting sequences and terminators available as appropriate regulatory sequences for the gene of interest. The selectable marker may be chosen from genes that confer antibiotic resistance to agents such as genticin, or positive selectable markers such as phosphomannose isomerase, which allows mannose to be used as a carbon source in cells which express the phosphomannose isomerase.

Any of the RNAi constructs can be transformed into sugarcane to generate transgenic plants using the above described protocol. *Agrobacterium* mediated genetic transformation is also possible and methods are described in the literature such as Arencibia, Ariel D. and Carmona, Elva R. Sugarcane (*Saccharum* spp.) Methods in Molecular Biology (Totowa, N.J., United States) (2006), 344(*Agrobacterium* Protocols (2nd Edition), Volume 2), 227-235; Manickavasagam et al (2004) Plant Cell Report 23:134-143; Snyman et al. (2006) Plant Cell Report 25: 1016-1023; Santosa et al. (2004) Molecular Biotechnology 28:113-119; and Gill et al. (2006) Plant Cell, Tissue and Organ Culture 84:227-231 herein all incorporated by reference.

That which is claimed:

1. A method for increasing starch content in green tissues of a plant comprising:
   a) inserting an expression cassette into a plant cell comprising a polynucleotide operably linked to a regulatory element that ensures transcription in plant cells, wherein expression of the polynucleotide inhibits or suppresses the expression of one or more endogenous starch degradation enzymes in green tissues selected from the group consisting of chloroplastic alpha amylase, glucan water dikinase, phosphoglucan water dikinase, limit dextrinase, isoamylase, chloroplastic beta-amylase, chloroplastic glucan phosphorylase, disproportionating enzyme, chloroplastic maltose transporter protein (Mex1), chloroplastic glucose transporter protein, and chloroplastic triose phosphate transporter protein, and wherein said regulatory element is a phosphoenol pyruvate carboxylase promoter and the plant cell is of a plant selected from the group consisting of maize, sugarcane, sorghum, millet, and switchgrass;
   b) regenerating transgenic plants from the plant cell of a); and
   c) producing said green tissue with increased starch content.

2. The method of claim 1, wherein said plant is an energy crop.

3. A method of improving the yield of free sugars from plant biomass for a biomass conversion method, said method comprising:
   a) inserting an expression cassette into a plant cell comprising a polynucleotide operably linked to a regulatory element that ensures transcription in plant cells, wherein expression of the polynucleotide inhibits or suppresses the expression of one or more endogenous starch degradation enzymes in green tissues selected from the group consisting of chloroplastic alpha amylase, glucan water dikinase, phosphoglucan water dikinase, limit dextrinase, isoamylase, chloroplastic beta-amylase, chloroplastic glucan phosphorylase, disproportionating enzyme, chloroplastic maltose transporter protein (Mex1), chloroplastic glucose transporter protein, and chloroplastic triose phosphate transporter protein, and wherein said regulatory element is a phosphoenol pyruvate carboxylase promoter and the plant cell is of a plant selected from the group consisting of maize, sugarcane, sorghum, millet, and switchgrass;
   b) regenerating transgenic plants from the plant cell of a);
   c) growing said transgenic plants under conditions in which the polynucleotide is expressed, wherein expression of the polynucleotide results in an increase in starch content in green tissues of said plant, and d) processing said transgenic plant in a biomass conversion method.

4. The method of claim 3, wherein said plant is an energy crop.

5. The method of claim 3, wherein said biomass conversion method is a non-animal feed biomass conversion method.

6. The method of claim 5, wherein said non-animal feed biomass conversion method converts carbohydrates to one or more biofuels.

7. A method of increasing biomass storage stability of dried plant tissue comprising:
- a) inserting an expression cassette into a plant cell comprising a polynucleotide operably linked to a regulatory element that ensures transcription in plant cells, wherein expression of the polynucleotide inhibits or suppresses the expression of one or more endogenous starch degradation enzymes in green tissues selected from the group consisting of chloroplastic alpha amylase, glucan water dikinase, phosphoglucan water dikinase, limit dextrinase, isoamylase, chloroplastic beta-amylase, chloroplastic glucan phosphorylase, disproportionating enzyme, chloroplastic maltose transporter protein (Mex1), chloroplastic glucose transporter protein, and chloroplastic triose phosphate transporter protein, wherein said regulatory element is a phospohenol pyruvate carboxylase promoter and the plant cell is of a plant selected from the group consisting of sugarcane and sorghum;
- b) regeneration of transgenic plants from the plant cell of a); and
- c) harvesting and drying of plant biomass from said transgenic plants.

8. The method of claim 7, wherein said plant is an energy crop.

9. A method for increasing starch content in green tissues of a plant comprising:
- a) inserting an expression cassette into a plant cell comprising a polynucleotide operably linked to a regulatory element that ensures transcription in plant cells, wherein expression of the polynucleotide inhibits or suppresses the expression of one or more endogenous starch degradation enzymes in green tissues selected from the group consisting of chloroplastic alpha amylase, glucan water dikinase, phosphoglucan water dikinase, limit dextrinase, isoamylase, chloroplastic beta-amylase, chloroplastic glucan phosphorylase, disproportionating enzyme, chloroplastic maltose transporter protein (Mex1), chloroplastic glucose transporter protein, and chloroplastic triose phosphate transporter protein, and wherein said regulatory element is a phospohenol pyruvate carboxylase promoter and the plant cell is of a plant selected from the group consisting of maize, sugarcane, sorghum, millet, and switchgrass;
- b) inserting a second expression cassette into said plant cell comprising a second polynucleotide operably linked to a regulatory element that ensures transcription in plant cells, wherein the second polynucleotide encodes a processing enzyme;
- c) regenerating transgenic plants from the plant cell of b); and
- d) producing said green tissue with increased starch content.

10. The method of claim 9, wherein the processing enzyme is an alpha-amylase.

11. The method of claim 1, wherein expression of the polynucleotide inhibits or suppresses the expression of glucan water dikinase.

12. The method of claim 3, wherein expression of the polynucleotide inhibits or suppresses the expression of glucan water dikinase.

13. The method of claim 7, wherein expression of the polynucleotide inhibits or suppresses the expression of glucan water dikinase.

14. The method of claim 9, wherein expression of the polynucleotide inhibits or suppresses the expression of glucan water dikinase.

* * * * *

SEQUENCE LISTING

```
<160> NUMBER OF SEQ ID NOS: 3

<210> SEQ ID NO 1
<211> LENGTH: 500
<212> TYPE: DNA
<213> ORGANISM: zea mays

<400> SEQUENCE: 1
agggcgtgct gcaggcggcc gtccagggcg agctgtggcg catgaaggac ggcaacggca      60
aggcgcccgg gatgatcggc tggctgccgg agaaggccgt cacgttcgtc gacaaccacg     120
acaccggctc cacgcagaac tcgtggccat tcccctccga caaggtcatg cagggctacg     180
cctatatcct cacgcaccca ggaactccat gcatcttcta cgaccacgtt ttcgactgga     240
acctgaagca ggagatcagc gcgctgtctg cggtgaggtc aagaaacggg atccacccgg     300
ggagcgagct gaacatcctc gccgccgacg gggatctcta cgtcgccaag attgacgaca     360
aggtcatcgt gaagatcggg tcacggtacg acgtcgggaa cctgatcccc tcagacttcc     420
acgccgttgc ccctggcaac aactactgcg tttgggagaa gcacggtctg agagttccag     480
cggggcggca ccactccgag                                                 500

<210> SEQ ID NO 2
<211> LENGTH: 500
```

```
-continued

<212> TYPE: DNA
<213> ORGANISM: zea mays

<400> SEQUENCE: 2
gctacagaac catagcacac atgctcacaa ggcatcgtgc tagcatgaac ttcacttgtg      60
ctgagatgag ggacagtgaa cagagttcag aggcgaaaag tgcacctgag gaactggttc     120
aacaggtgct gagtgctgga tggagagagg gcctaaattt ggcatgtgaa aatgcactca     180
accgatatga tgcaacagct tacaacacca tcctcaggaa tgcaagacct caaggcatca     240
acaagaatgg ccctccagaa cacaagttgc acggattcac ctacctccga gtatctgatg     300
aactgttcca ggaacagaac tacaccactt tcaaaacttt tgtcaggaga atgcatgcta     360
acctggatta taatccaaat gtcgatccag ttgcaccatt ggaaagatca aaggcagaga     420
taccaattga agaaatccta gaagtagcac agccaaaatt ggagccattt cccttcgaca     480
aggacaccga cctaccagtt                                                500

<210> SEQ ID NO 3
<211> LENGTH: 330
<212> TYPE: DNA
<213> ORGANISM: zea mays

<400> SEQUENCE: 3
gatgaccttg actctcccaa gttacttggt tacccaagca agccaattgg tctcttcata      60
aggcaatcaa tcatcttccg ttccgactcc aacggtgagg acctggaagg ttatgctgga    120
gcaggattat atgatagcgt accgatggat gaggaggatg aggttgtact tgattacaca    180
actgaccctc ttatagtaga ccgtggattc cgaagctcaa tcctctcaag catagcacgg    240
gctggccatg ccatcgagga gctatacggt tctcctcagg acgtcgaggg agtagtgaag    300
gatggaaaaa tctatgtagt ccagacaaga                                     330
```